United States Patent [19]

Miyazawa et al.

[11] Patent Number: 5,779,936
[45] Date of Patent: Jul. 14, 1998

[54] LIQUID CRYSTALLINE COMPOUND AND LIQUID CRYSTAL COMPOSITION CONTAINING THE SAME

[75] Inventors: Kazutoshi Miyazawa; Shuichi Matsui; Atsuko Fujita; Tomoyuki Kondo; Yasuyuki Goto; Etsuo Nakagawa; Shinichi Sawada, all of Chiba, Japan

[73] Assignee: Chisso Corporation, Osaka, Japan

[21] Appl. No.: 682,678

[22] PCT Filed: Nov. 11, 1994

[86] PCT No.: PCT/JP94/01914

§ 371 Date: Jul. 24, 1996

§ 102(e) Date: Jul. 24, 1996

[87] PCT Pub. No.: WO95/20021

PCT Pub. Date: Jul. 27, 1995

[30] Foreign Application Priority Data

Jan. 25, 1994 [JP] Japan .................... 6-6629
Jun. 10, 1994 [JP] Japan .................... 6-129304

[51] Int. Cl.⁶ .................... C09K 19/30; C07C 22/08
[52] U.S. Cl. .................... 252/299.63; 252/299.01; 570/131
[58] Field of Search .................... 252/299.01, 299.61, 252/299.63, 299.66; 570/131

[56] References Cited

U.S. PATENT DOCUMENTS 5,198,151 3/1993 Kurataki et al. .................... 252/299.66
5,516,454 5/1996 Scheuble et al. .................... 252/299.01

OTHER PUBLICATIONS

CA 118:91036, 1992
CA 117:101196, 1992.
CA 116:184669, 1991.
CA 115:146735, 1991.
*Chemical Abstract* 122:132748, 1993.

*Primary Examiner*—Shean C. Wu
*Attorney, Agent, or Firm*—Wenderoth, Lind & Ponack, L.L.P.

[57] ABSTRACT

A liquid crystalline compound expressed by the general formula (1)

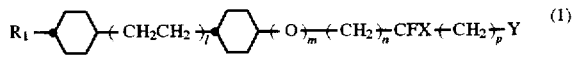

(wherein $R_1$ is an alkyl group having 1 to 12 carbon atoms and one $CH_2$ group in the alkyl group may be replaced by oxygen atom or —CH=CH—; X represents hydrogen atom or fluorine atom; Y represents hydrogen atom or alkoxy group having 1 to 5 carbon atoms; l and m independently represent 0 or 1, respectively; and n and p independently represent an integer of 0 to 10, respectively, and when p is 0, n is 1 or more, and when Y is an alkoxy group, X is a fluorine atom and p is 0.)

Liquid crystal compositions which are suitable for use in liquid crystal display devices, have a high clearing point, and have a function of decreasing viscosity, and novel liquid crystalline compounds useful as a component of the liquid crystal compositions are provided.

16 Claims, No Drawings

LIQUID CRYSTALLINE COMPOUND AND LIQUID CRYSTAL COMPOSITION CONTAINING THE SAME

This application is a 371 of PCT/JP94/01914 filed Nov. 11, 1994.

FIELD OF TECHNOLOGY

The present invention relates to a liquid crystalline compound and liquid crystal composition. More specifically, the present invention relates to a novel liquid crystalline compound having a group substituted with fluorine at the end of the molecule and a liquid crystal composition containing the same.

BACKGROUND TECHNOLOGY

Liquid crystal compositions, particularly nematic liquid crystal compositions are widely used for display materials, for example, in displays such as watches, tabletop calculators, word-processors, computer terminals, and televisions. Driving mode of liquid crystal display devices using a nematic liquid crystal composition is roughly classified into three kinds of modes such as twisted nematic (TN), super twisted nematic (STN), and thin film transistor driving.

While a suitable driving mode is selected according to application, it is necessary in any method that response speed to field inversion is high to realize an excellent displaying capability.

In order to actualize a high response speed to field, it is necessary that the viscosity of liquid crystal composition is low. That is, it is important to use a liquid crystal composition having a low viscosity. In order to achieve this object, attempts have been made in which a bicyclohexane type compound or cyclohexylethyl cyclohexane type compound which is known as a low viscosity liquid crystal compound is used as a constituent (hereinafter referred to as viscosity decreasing agent) of liquid crystal compositions to decrease the viscosity (for example, Examined Japanese Patent Publication No. 05-020418, Examined Japanese Patent Publication No. 62-015052, Unexamined Japanese Patent Publication No. 59-70624, and WO 90/01056). However, such bicyclic cyclohexane type compounds have a disadvantage that clearing point (temperature at which a liquid crystal phase or crystal becomes an isotropic liquid) is low. When the decrease in viscosity of the compositions is intended, the amount of viscosity decreasing agent to be used is as much as several tens percent, and as the result, mesomorphic range of liquid crystal compositions is remarkably decreased. Consequently, it is conceivable to start from bicyclohexane type compounds or cyclohexylethyl cyclohexane type compounds having a function of decreasing viscosity and deriving them to liquid crystalline compounds which additionally have a high clearing point. However, efficient methods for the derivation have not yet been known.

Heretofore, compounds in which fluorine atoms are introduced in such a group as a side chain alkyl group at the end of a molecule, for example, compounds in which three or more fluorine atoms are introduced in a side chain alkyl group (DE 4101600), compounds in which a plural number of difluoromethylene groups are introduced (DE 4034123), and compounds in which fluorine atoms are introduced at the central bonding part (DE 4023106 and DE 4015681) are known. However, these compounds are not related to bicyclohexane type compounds nor cyclohexylethyl cyclohexane type compounds. Besides, these compounds do not lead to a rise in the clearing point.

Further, there have been proposed many applications in which compounds having a fluoroalkyl group are recited in their claims (for example, Unexamined Japanese Patent Publication Nos. 1-135745 and 3-153670). However, there is no case in which such compounds are actually prepared and their physical properties of the compounds are studied.

DISCLOSURE OF THE INVENTION

An object of the present invention is to overcome the defects in the prior art mentioned above and to provide bicyclohexane type compounds or cyclohexylethyl cyclohexane compounds which can raise the clearing point of liquid crystal compositions while maintaining viscosity decreasing function when used as a component of liquid crystal compositions, and to provide liquid crystal compositions containing the compounds.

The present invention which is to achieve the objects mentioned above and claimed by the present application is summarized as follows:

(1) A liquid crystalline compound expressed by the general formula (1)

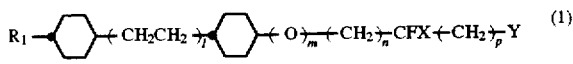

(wherein $R_1$ is an alkyl group having 1 to 12 carbon atoms and one $CH_2$ group in the alkyl group may be replaced by oxygen atom or —CH=CH—; X represents hydrogen atom or fluorine atom; Y represents hydrogen atom or alkoxy group having 1 to 5 carbon atoms; Q and m independently represent 0 or 1, respectively; and n and p independently represent an integer of 0 to 10, respectively, and when p is 0, n is 1 or more, and when Y is an alkoxy group, X is fluorine atom and p is 0.)

(2) A liquid crystalline compound recited in (1) wherein m is 0.

(3) A liquid crystalline compound recited in (1) wherein m is 1.

(4) A liquid crystalline compound recited in (1) wherein Y is hydrogen atom.

(5) A liquid crystalline compound recited in (1) wherein Y is an alkoxy group.

(6) A liquid crystalline compound recited in (2) wherein p is 0.

(7) A liquid crystalline compound recited in (2) wherein p is 1.

(8) A liquid crystalline compound recited in (3) wherein p is 0.

(9) A liquid crystalline compound recited in (3) wherein p is 1.

(10) A liquid crystal composition comprising two or more components and containing, as component, at least one compound recited in any one of the items (1) to (9) mentioned above.

(11) A liquid crystal composition containing, as a first component, at least one compound recited in any one of the items (1) to (9) mentioned above and containing, as a second component, one or more compounds selected from the group consisting of the following general formulas (II), (III), and (IV)

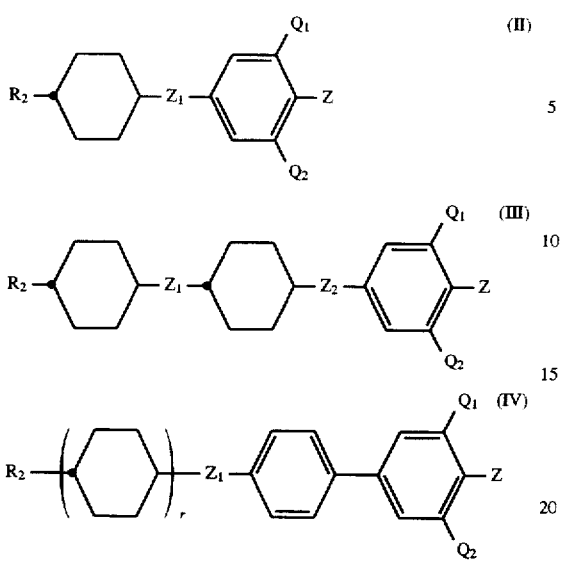

(wherein $R_2$ represents an alkyl group having 1 to 10 carbon atoms, Z represents F or Cl, $Q_1$ and $Q_2$ independently represent H or F, respectively, r represents 1 or 2, and $Z_1$ and $Z_2$ independently represent —CH$_2$CH$_2$— or covalent bond.)

(12) A liquid crystal composition containing, as a first component, at least one compound recited in any one of the items (1) to (9) mentioned above, and containing, as a second component, one or more compounds selected from the group consisting of the following general formulas (V), (VI), (VII), (VIII), and (IX)

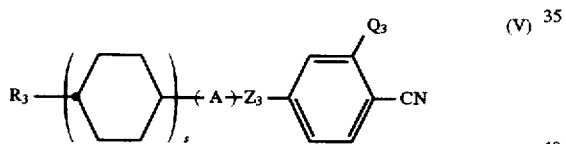

(wherein $R_3$ represents an alkyl group having 1 to 10 carbon atoms or an alkenyl group having 2 to 10 carbon atoms, methylene groups which are not adjacent to each other in these groups may be replaced by oxygen atom, $Z_3$ represents —CH$_2$CH$_2$—, —COO—, or covalent bond, $Q_3$ represents H or F, A represents a cyclohexane ring, benzene ring, or 1,3-dioxane ring, and s represents 0 or 1.)

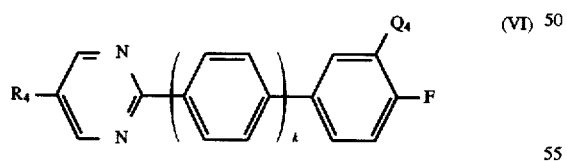

(wherein $R_4$ represents an alkyl group having 1 to 10 carbon atoms, $Q_4$ represents H or F, and k represents 0 or 1.)

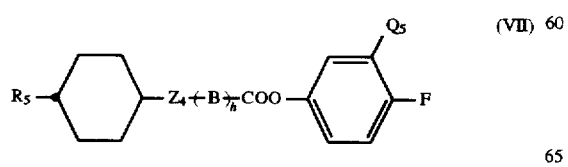

(wherein $R_5$ represents alkyl group having 1 to 10 carbon atoms, B represents cyclohexane ring or benzene ring, $Q_5$ represents H or F, $Z_4$ represents —COO— or covalent bond, and h represents 0 or 1.)

(wherein $R_6$ and $R_7$ independently represent an alkyl group, alkoxy group, or alkoxymethyl group each having 1 to 10 carbon atoms, K represents cyclohexane ring, pyrimidine ring, or benzene ring, D represents cyclohexane ring or benzene ring, and $Z_5$ represents —C≡C—, —COO—, —CH$_2$CH$_2$—, or covalent bond.)

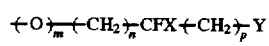

(wherein $R_8$ represents an alkyl group or alkoxy group each having 1 to 10 carbon atoms, $R_9$ represents an alkyl group, alkoxy group, or alkoxymethyl group each having 1 to 10 carbon atoms, E represents cyclohexane ring or pyrimidine ring, G and J independently represent cyclohexane ring or benzene ring, respectively, $Z_6$ independently represents —COO—, —Ch$_2$CH$_2$—, or covalent bond, respectively, $Z_7$ represents —C≡C—, —COO—, or covalent bond, and $Q_6$ represents H or F.)

(13) A liquid crystal display device composed by using a liquid crystal composition comprising 2 or more components and containing, as component, at least one compound recited in any one of the items (1) to (9) mentioned above.

(14) A liquid crystal display device composed by using a liquid crystal composition recited in any one of the items (10) to (12) mentioned above.

BEST MODE FOR CONDUCTING THE INVENTION

Liquid crystalline compounds expressed by the general formula (1) in the present invention are characterized by having a fluoroalkyl or fluoroalkoxy group expressed by the following formula at the end of the molecule:

$$(O)_m(CH_2)_n CFX(CH_2)_p Y$$

(wherein m, n, p, X, and Y are the same as those mentioned above).

Clearing point is raised by introducing the group mentioned above at the end of the molecule. Among the compounds of the formula (1), ones exhibiting particularly preferable characteristics are roughly classified into the following 10 groups of (1a) to (1k):

| | |
|---|---|
| Q(CH$_2$)$_n$CF$_2$(CH$_2$)$_q$H | (1a) |
| Q(CH$_2$)$_n$CF$_2$H | (1b) |
| Q(CH$_2$)$_n$CFH(CH$_2$)$_q$H | (1c) |
| Q(CH$_2$)$_n$CFH$_2$ | (1d) |
| Q—O(CH$_2$)$_n$CF$_2$(CH$_2$)$_q$H | (1e) |
| Q—O(CH$_2$)$_n$CF$_2$H | (1f) |
| Q—O(CH$_2$)$_n$CFH(CH$_2$)$_q$H | (1g) |
| Q—O(CH$_2$)$_n$CFH$_2$ | (1h) |

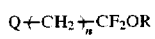

(wherein n is the same as that mentioned above, R is an alkyl group having 1 to 5 carbon atoms, q is an integer of 1 to 10, Q is 4-(4-substituted cyclohexyl)cyclohexyl group or 4-(2-(4-substituted cyclohexyl)ethyl)cyclohexyl group.)

That is, the compounds of the present invention are roughly classified, in reference to the substituent at the end of the molecule mentioned above, into groups (1a) and (1e) which have a difluoromethylene group within alkyl groups or alkoxy groups; (1b) and (1f) which have a difluoromethyl group at the end; (1c) and (1g) which have a monofluoromethylene group in the substituent group; (1d) and (1h) which have a monofluoromethyl group at the end; and (1j) and (1k) which have an alkoxy substituted difluromethyl group at the end.

Most of the compounds of the present invention exhibit a smectic phase. Whereas liquid crystal compositions used for display devices are ones having a nematic phase, when mixed with nematic liquid crystal compounds, the compounds of the present invention do not produce such injurious effects as of decreasing the temperature range of nematic phase. Thus, the compounds of the present invention are suitable and preferable as constituent for nematic liquid crystal compositions.

Since the compounds of the present invention are extremely stable in chemical nature and not deteriorated by the effects of heat, ultraviolet ray, and electric field, they are preferable as a constituent of electrooptical devices.

Compounds expressed by the formula (1) in the present invention are produced by the following methods depending on the values and groups adopted for m, p, and X, respectively:

Abbreviations used in the description hereinafter have meanings as follows:

| | |
|---|---|
| DAST: | Diethylaminosulfur trifluoride |
| LAH: | Aluminum lithium hydride |
| SBH: | Sodium boron hydride |
| HFP-ET$_2$NH: | Hexafluoropropene diethylamine |
| DAIBAL: | Aluminum diisobutyl hydride |
| PCC: | Pyridiumchlorochromate |
| Lawson reagent: | 2,4-bis (4-methoxyphenyl)-1,3-dithia-2,4-diphosphethane-2,4-disulfide |
| PDC: | Pyridiumdichromate |

Production of the compounds ((1a) and (1c)) wherein m is 0, p or q is 1 or more, Y is hydrogen atom:

The compounds can be produced according to the following scheme:

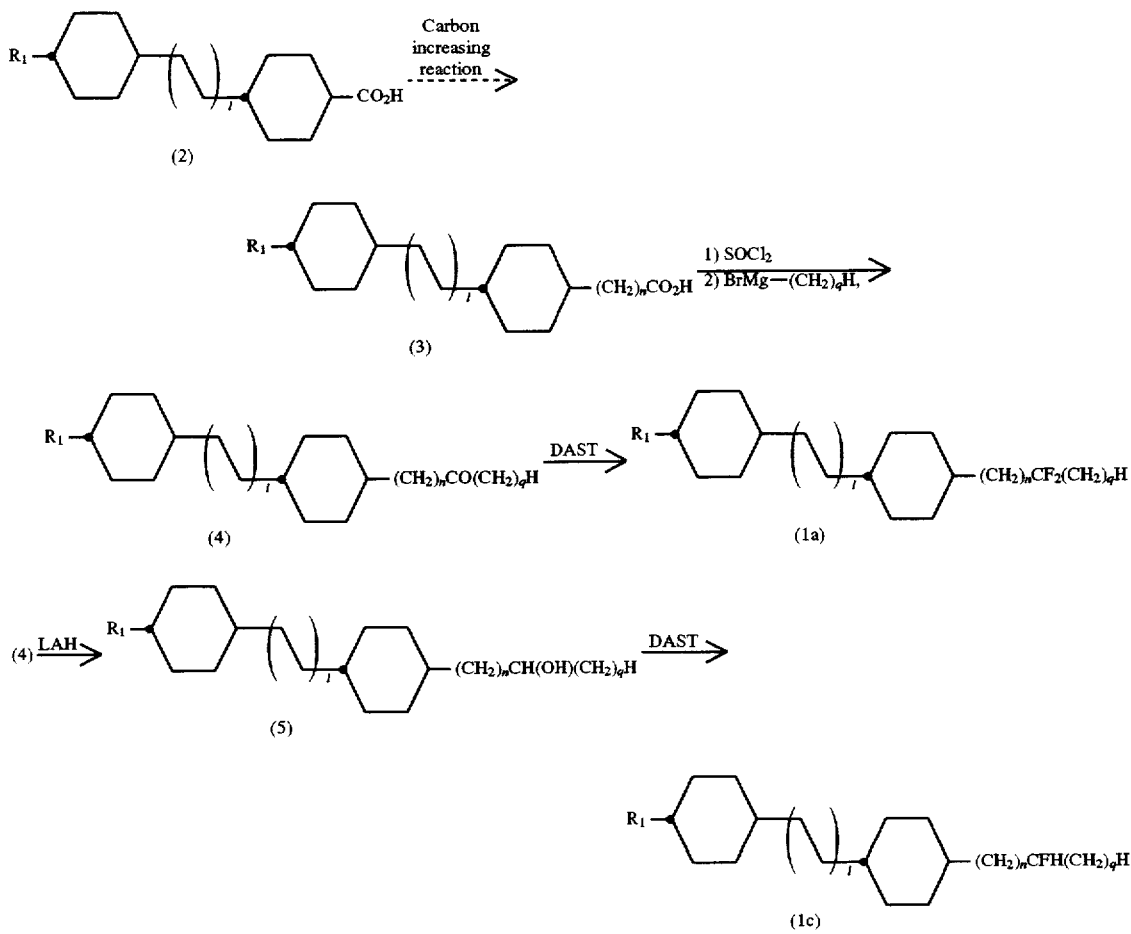

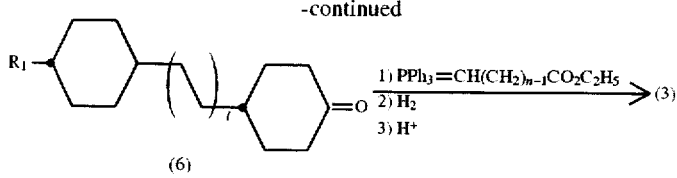

(In the description above, Q and n show the same meanings as described before.)

That is, when n is 1 or more, (3) is obtained by subjecting cyclohexane carboxylic acids (2) produced according to the method of Krause et al. (U.S. Pat. No. 4,229,315) to a carbon increasing reaction. A ketone (4) is obtained by converting (3) to an acid halide with a halogenating reagent such as thionyl chloride and reacting with alkylmagnesium halide in the presence of a catalyst according to a method of Fiandaneze et al. (Tetrahedron Letters, 25, 4805 (1984)). (4) is converted to a corresponding (1a) by reacting with a fluorinating agent such as DAST (W. H. Midleton et al., Journal of the Organic Chemistry, 40, 574 (1975)), MQF$_6$ (F. Massey et al., Tetrahedron, 31,391 (1975), SeF$_4$ (G. A. Oller et al., Journal of the American Chemical Society, 96, 925 (1974)), SF$_4$ (G. A. Bozwell et al., Organic Reactions, 21, 1 (1974)), and CF$_2$BR$_2$/Zn (C. M. Hume et al., Journal of the Chemical Society Parkin Trans, 1,335 (1993)). Fluorination of carbonyl groups can also be performed by converting carbonyl compounds to more reactive derivatives and fluorinating them. That is, methods passing through hydrazones (S. Rosen et al., Journal of the American Chemical Society, 109, 896 (1987), G. K. S. Plakash et al., Synlet, 594 (1990), T. B. Patrick, Journal of the Fluorine Chemistry, 157 (1983)), a method through diazo compounds (T. B. Patrick et al., Journal of the Organic Chemistry, 46, 3917 (1981)), a method through 1,3-dithiolane (S. C. Sonji et al., Journal of the Organic Chemistry, 51,3508 (1986)), and a method through geminaldihalogen compounds (A. J. Bladworth et al., Tetrahedron Letters, 5347 (1987)) are preferably used. On the other hand, when n is 0, (2) may be converted to a ketone (4) by directly converting (2) to an acid halide with a halogenating reagent such as thionyl chloride and then reacting with alkylmagnesium halide in the presence of a catalyst. Also, (1c) can be produced by reducing (4) with a reducing agent such as LAH and SBH to form an alcohol (5) and then fluorinating hydroxyl group with a fluorinating agent. In this case, DAST and HFP-ET$_2$NH are preferable as fluorinating agent to be used (N. Ishikawa et al., Bulletin Chemical Society of Japan, 52, 3377 (1979). Further, (3) can also be obtained by converting a cyclohexanone (6) to an unsaturated ester by Wittig reaction (for instance, O. Isler et al., Helvetica Chimica Acta, 40, 1242 (1957)) or by a method of Emmons et al. (Organic Synthesis V, 547 (1973)), and then subjecting unsaturated parts to a hydrogenation.

Production of the compounds ((1b) and (1d)) wherein m is 0, p is 0, and Y is a hydrogen atom:

The compounds can be produced according to the following scheme:

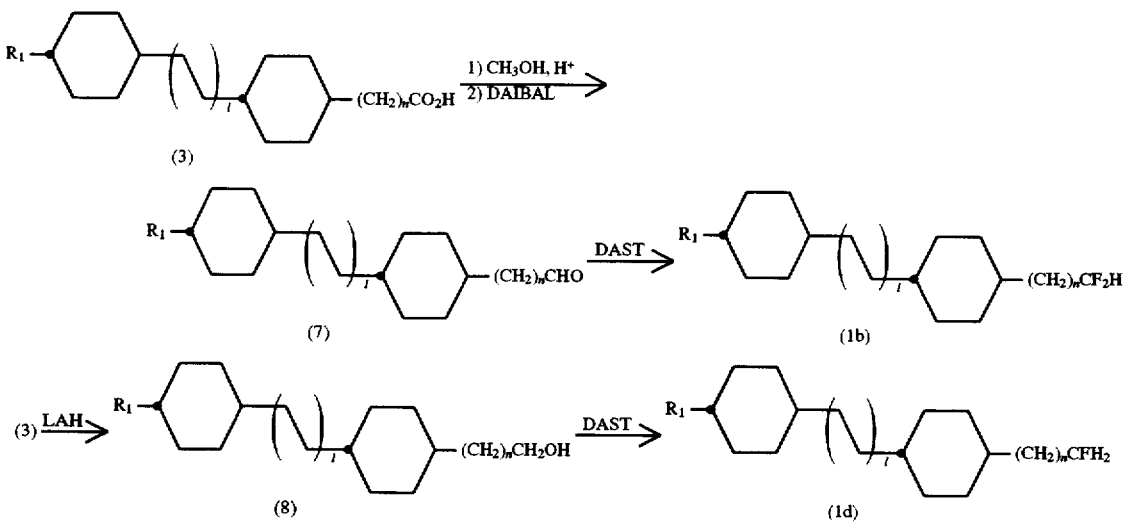

(In the description above, Q and n show the same meanings as described before.)

That is, (1b) is obtained be deriving a carboxylic acid (3) to an aldehyde (7) and then fluorinating it by the same method as mentioned before. Whereas (7) is preferably synthesized by using DAIBAL according to the method, for example, of Zakhalkin et al. (Tetrahedron Letters, 619 (1962)), it can also be obtained by reducing (3) to form an alcohol, and further oxidizing it with an oxidizing agent such as PCC. Further, (1d) can be produced by reducing (3) with a reducing agent such as LAH and SBH to form an alcohol (8) and then fluorinating a hydroxyl group with a fluorinating agent mentioned before.

Production of the compounds ((1e) and (1g)) wherein m is 1, p or q is 1 or more, and Y is hydrogen atom:

The compounds can be produced according to the following scheme:

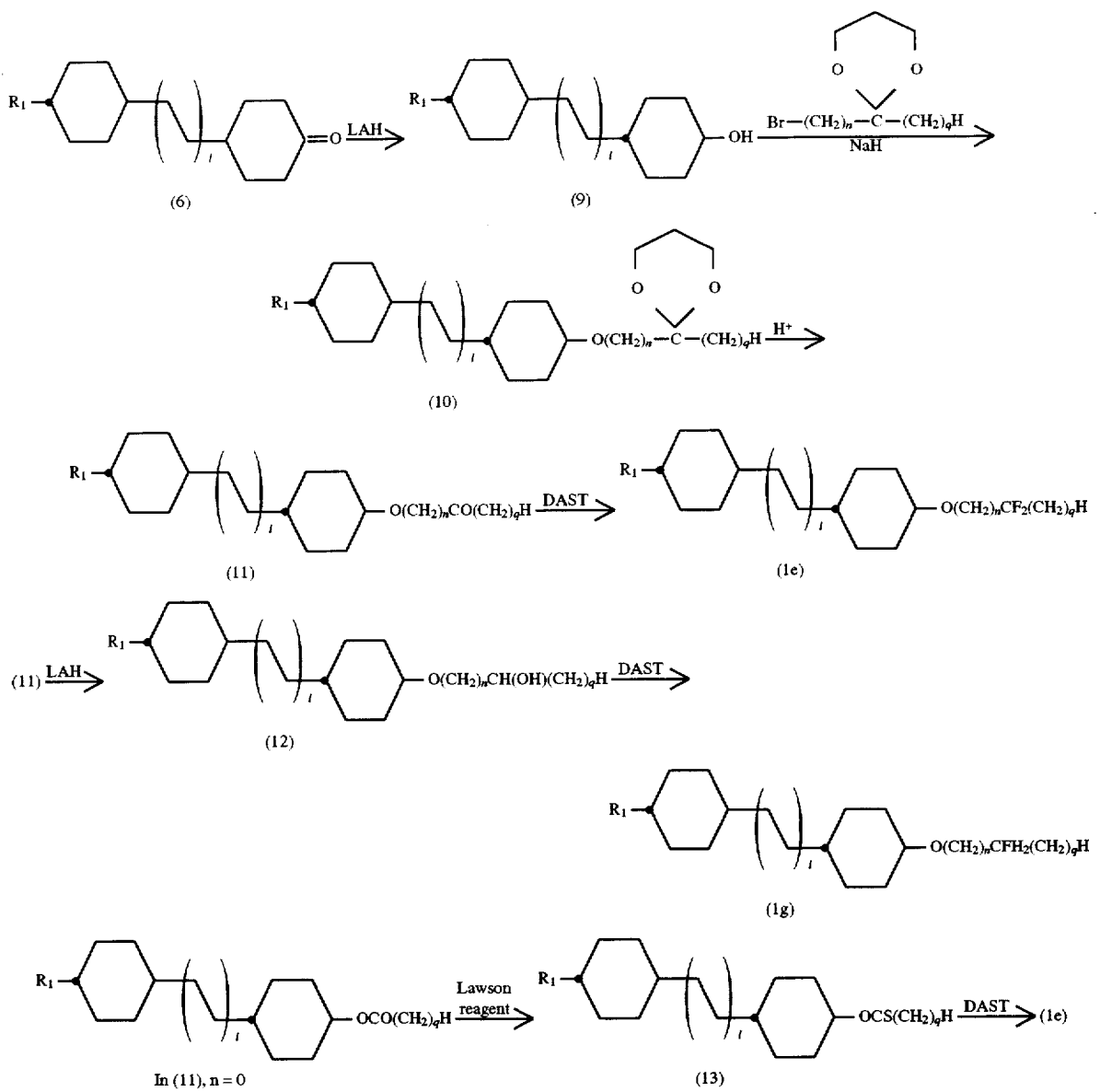

(In the description above. Q. n. and q show the same meanings as described before.)

That is, a ketal such as (10) is obtained by reducing a cyclohexanone derivative (6) with a reducing agent such as LAH and SBH to convert into a cyclohexal derivative (9) and then reacting with an alkyl halide. (1e) can be produced (when n is 1 or more) by separating a protective group to form (11) and then fluorinating it with a fluorinating agent mentioned before. Further, (1g) can be produced by reducing (11) with a reducing agent such as LAH and SBH to form an alcohol (12) and then fluorinating hydroxyl group with a fluorinating agent mentioned before. In this case, when n is 0, since (11) is an ester, it is preferable to convert it into a thioester (13) with a Lawson reagent (Synthesis, 941 (1979)) and then fluorinating it with DAST to obtain (1e).

Production of the compounds ((1f) and (1h)) wherein m is 1, p is 0, and Y is a hydrogen atom:

The compounds can be produced by the following scheme:

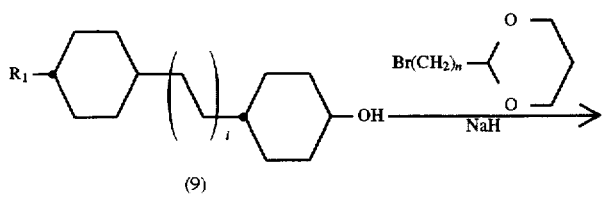

-continued

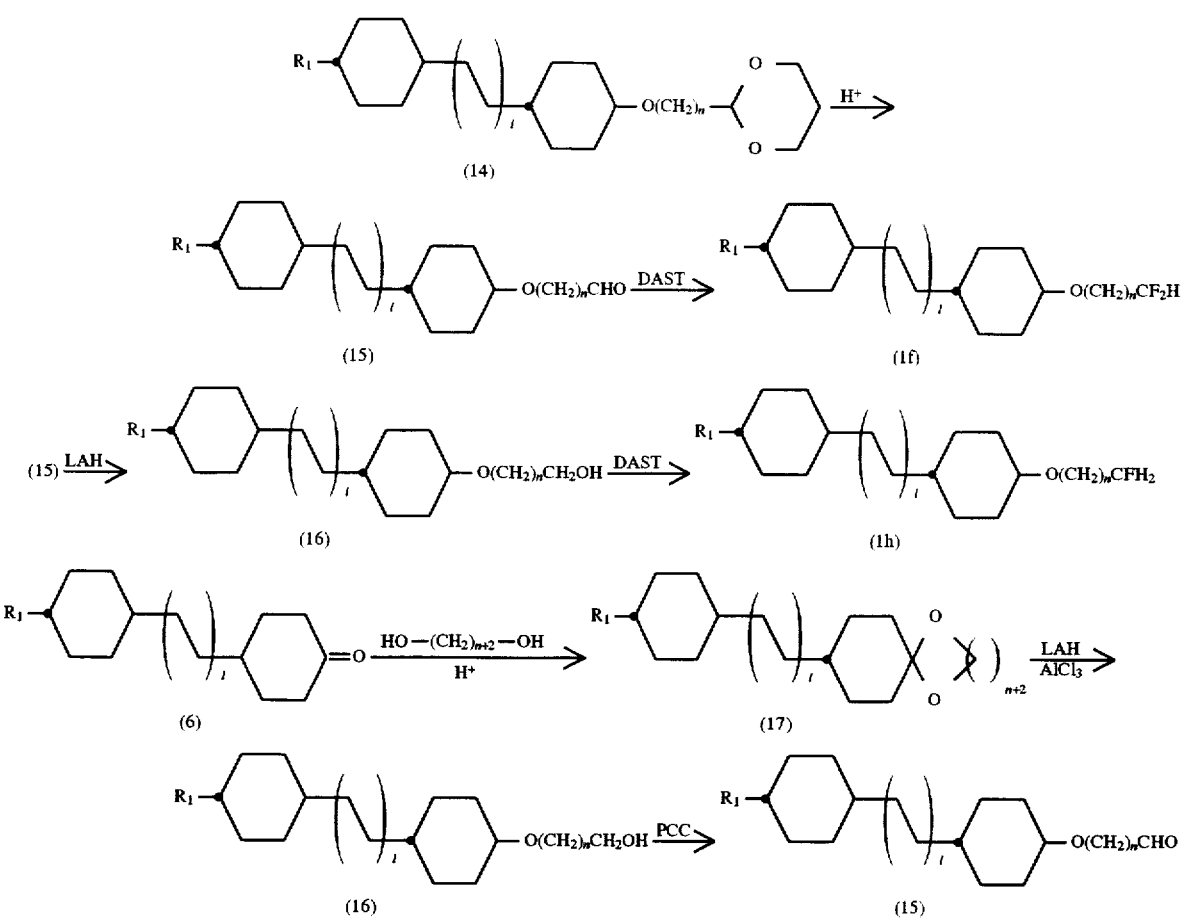

(In the description above, Q and n show the same meanings as described before.)

That is, (14) is obtained by reacting a cyclohexanol derivative (9) with an alkyl halide. (1f) can be produced by separating a protective group to convert it into an aldehyde (15) and then fluorinating with a fluorinating agent mentioned before. Further, (1h) can be produced by reducing (15) with a reducing agent such as LAH and SBH to form an alcohol (16) and then fluorinating hydroxyl group with a fluorinating agent mentioned before. When n is 1 or 2 in this procedure, as a different method, an alcohol (16) can be obtained by reacting a cyclohexanone derivative (6) with ethylene glycol or 1,3-propanediol to convert into a spiroketal (17) and then reducing it with LAH in the presence of a Lewis acid according to the method of Dygenote et al. (Organic Synthesis V. 303 (1973)). Further, an aldehyde (15) can be obtained by oxidizing (16) with PCC or another compound.

Production of the compounds ((ij) and (1k)) wherein m is 0 or 1, X is a fluorine atom, p is 0, and Y is an alkoxy group:

The compounds can be produced by the following scheme:

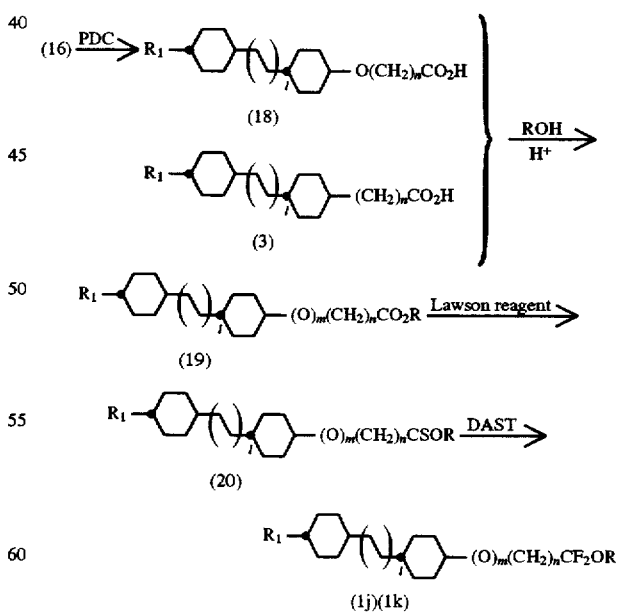

(In the description above, Q, n, and R show the same meanings as described before.)

That is, (20) is obtained by deriving a carboxylic acid (3) or carboxylic acid (18) obtained by oxidizing an alcohol (16)

with PDC to an ester (19), and then treating it with a Lawson reagent. (1j) and (1k) are obtained by fluorinating (20) thus obtained with a fluorinating agent mentioned before.

Compounds (1) of the present invention produced by such methods mentioned above are remarkably excellent as constituent for nematic liquid crystal compositions. That is, the compounds can provide nematic liquid crystal compositions suitable for electrooptical devices since the compounds have excellent characteristics mentioned before and besides, they are readily miscible with several liquid compounds. Such liquid crystal compositions are preferably achieved by mixing a compound optionally selected, depending on the purpose, from a group of compounds (B) having a Δε of ≧5, a group of compounds (C) having a |Δε| of <5, particularly a group of compounds (D) having a clearing point of 80° C. or higher, and a group of other compounds (E) to a component (A) containing at least one compounds (1).

Following compounds can preferably be mentioned as ones included in (B), (C), (D), or (E). That is, the following (B1) to (B13) can be stated first as the compounds included in (B):

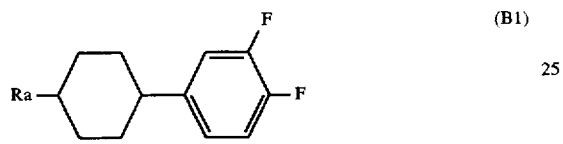 (B1)

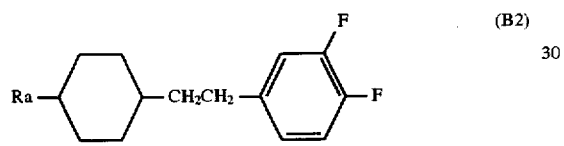 (B2)

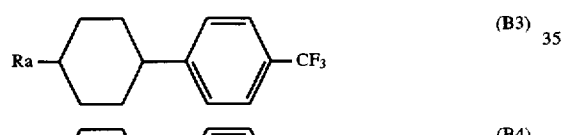 (B3)

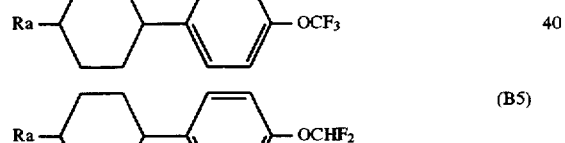 (B4)

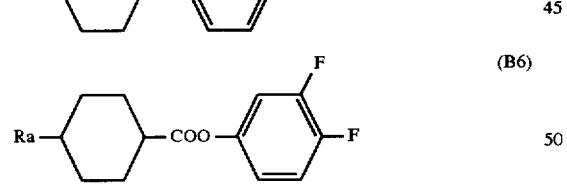 (B5)

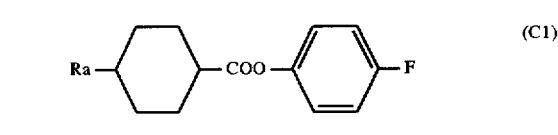 (B6)

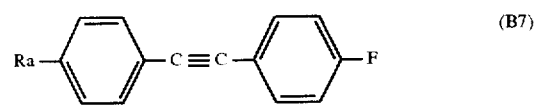 (B7)

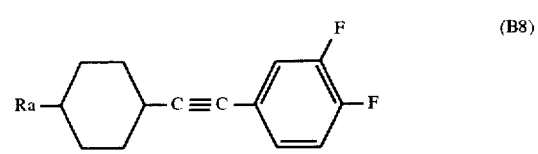 (B8)

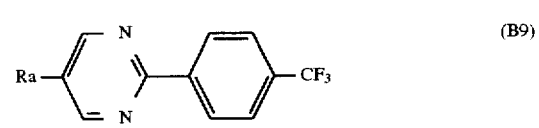 (B9)

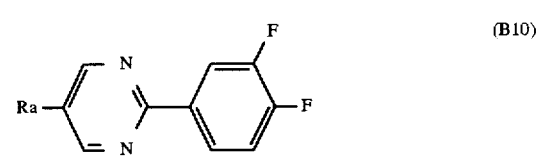 (B10)

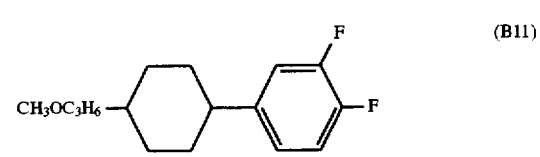 (B11)

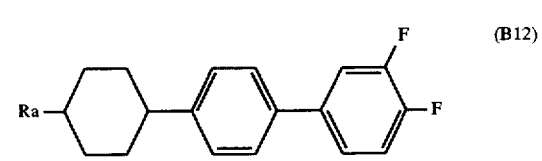 (B12)

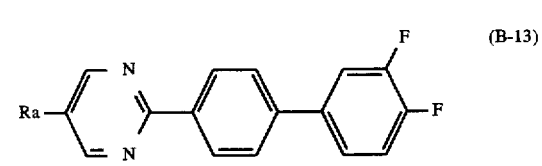 (B-13)

(In the description above, whereas Ra represents an alkyl group or alkenyl group having 1 to 10 carbon atoms, a carbon atom, or two or more carbon atoms which are not adjacent to each other in the group may be substituted with oxygen atom.)

The following (C1) to (C34) can be mentioned as the compounds corresponding to (C):

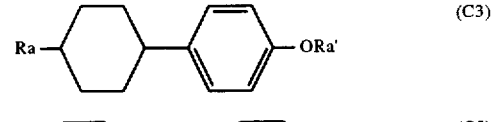 (C1)

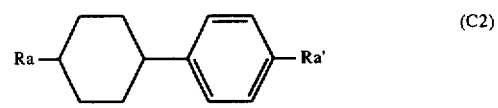 (C2)

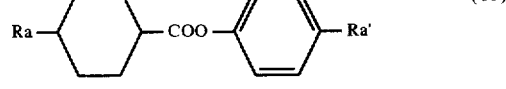 (C3)

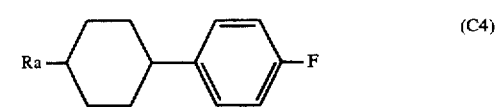 (C4)

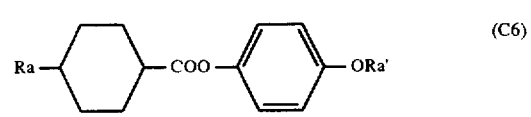 (C5)

(C6)

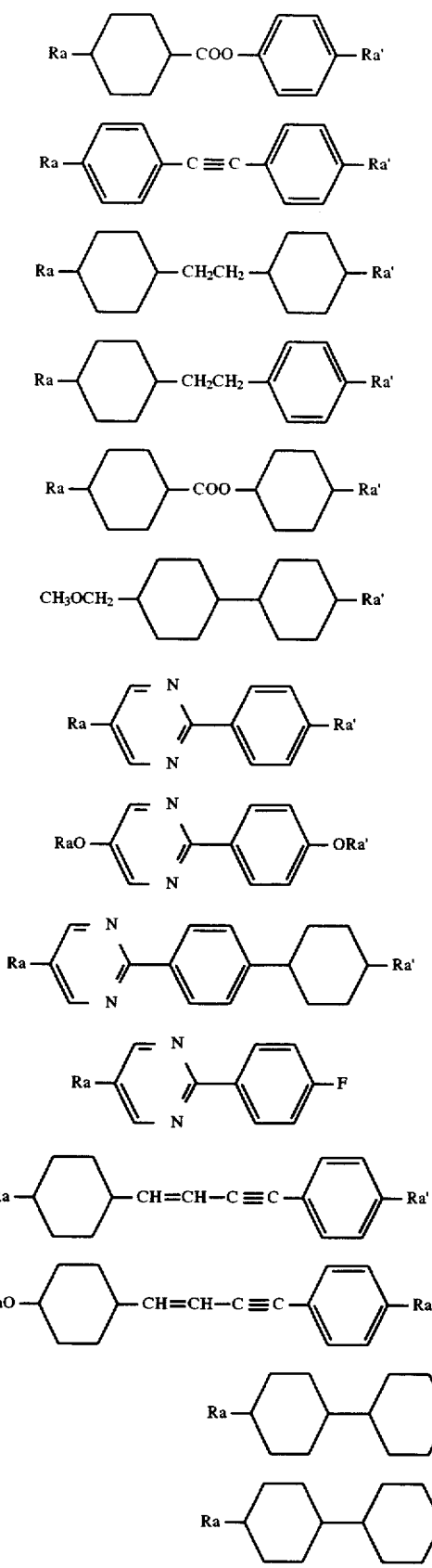
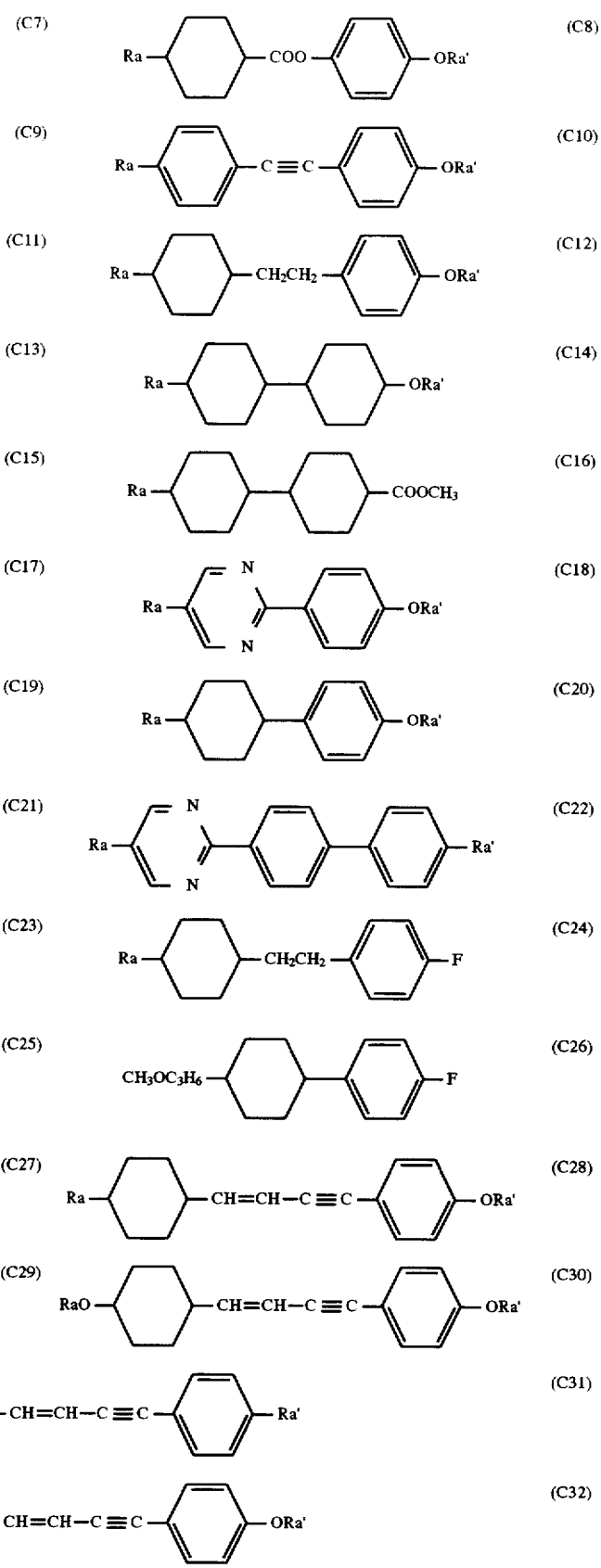

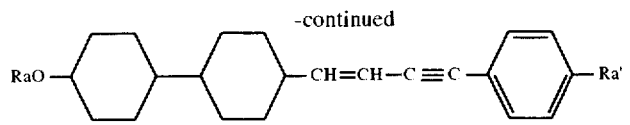
(C33)
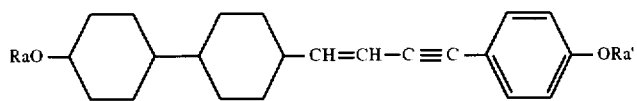
(C34)
(In the description above, whereas Ra and Ra' independently represents an alkyl group or alkenyl group having 1 to 10 carbon atoms, respectively, one carbon atom, or two or more carbon atoms which are not adjacent to each other in the group may be 5 substituted with oxygen atom.) The following (D1) to (D57) can be mentioned as the compounds corresponding to (D):
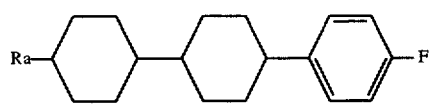
(D1)
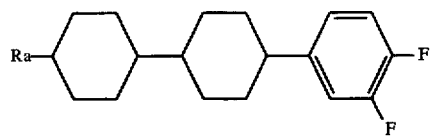
(D2)
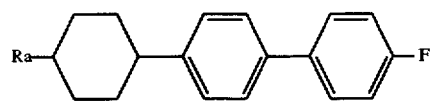
(D3)
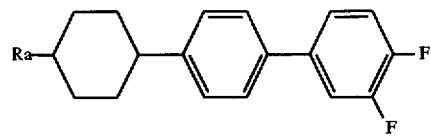
(D4)
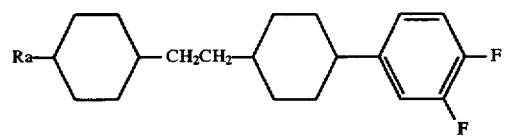
(D5)
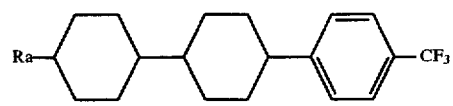
(D6)
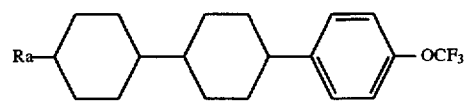
(D7)
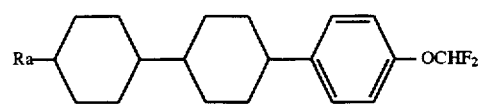
(D8)
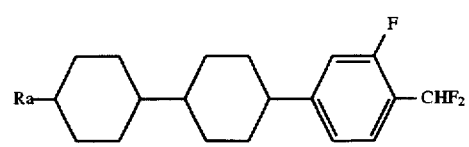
(D9)
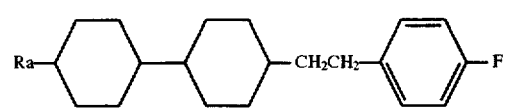
(D10)

-continued
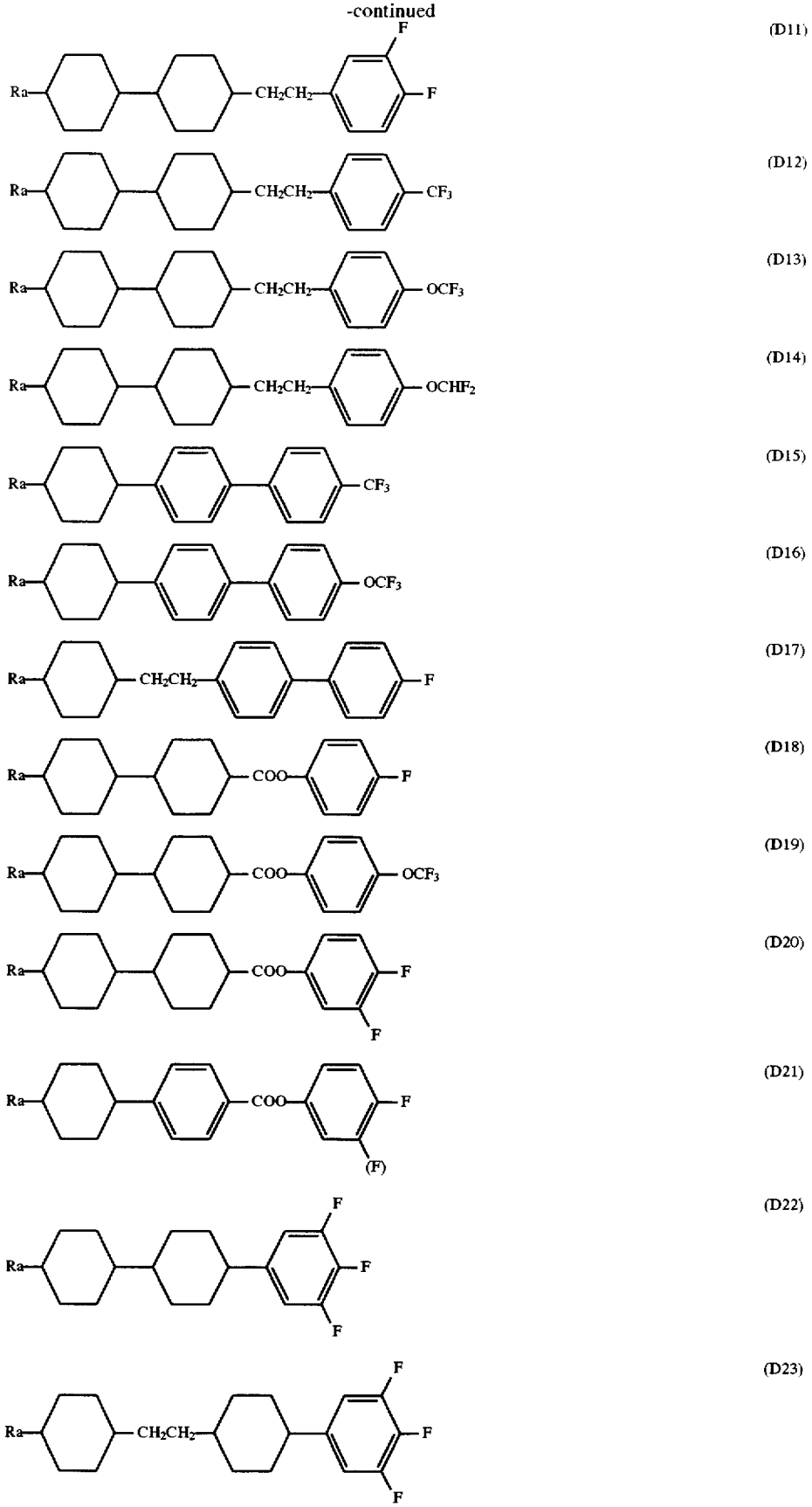

-continued
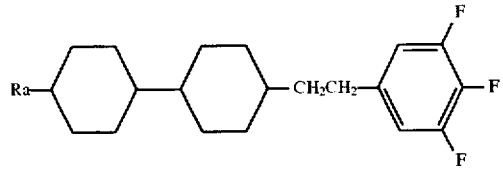 (D24)
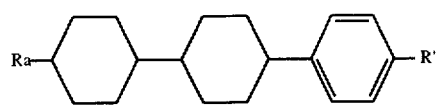 (D25)
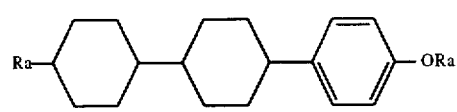 (D26)
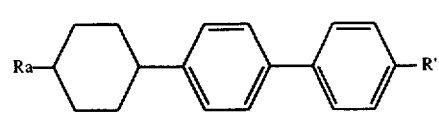 (D27)
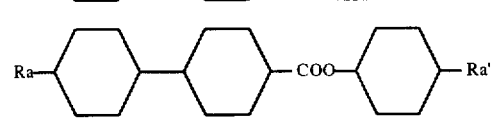 (D28)
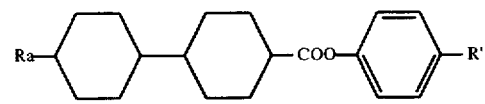 (D29)
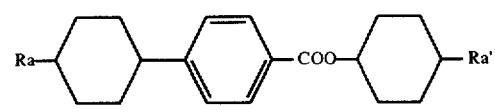 (D30)
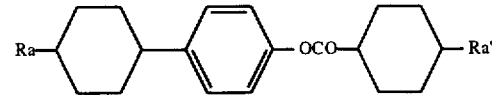 (D31)
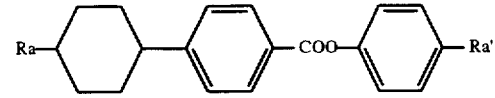 (D32)
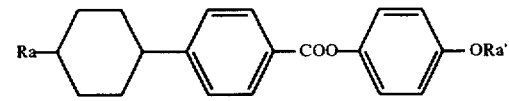 (D33)
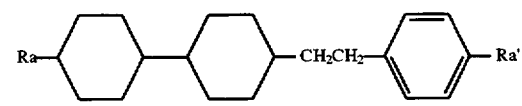 (D34)
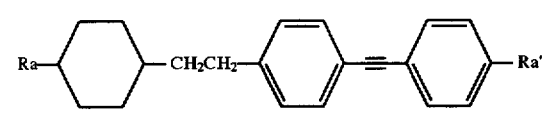 (D35)
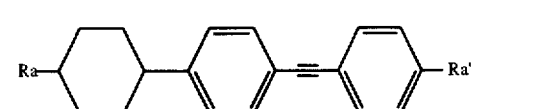 (D36)
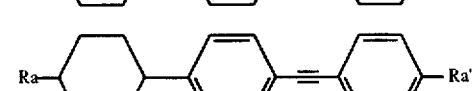 (D37)
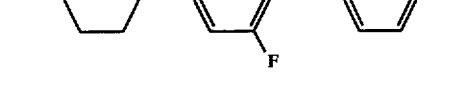

-continued
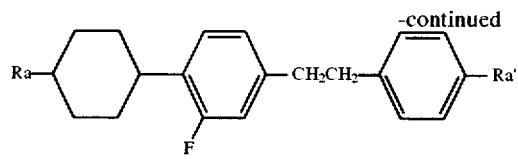 (D38)
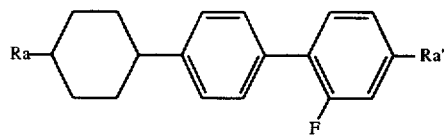 (D39)
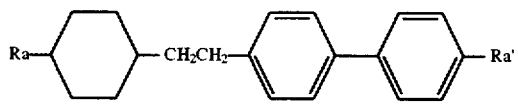 (D40)
 (D41)
 (D42)
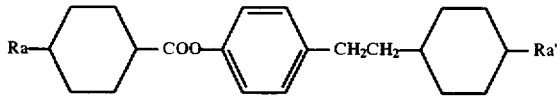 (D43)
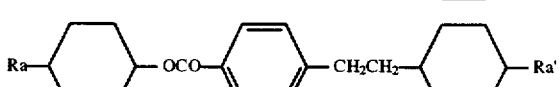 (D44)
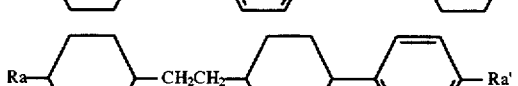 (D45)
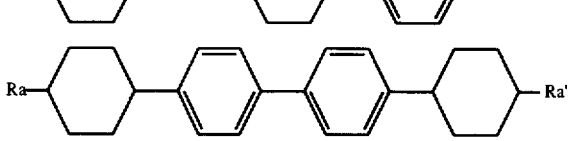 (D46)
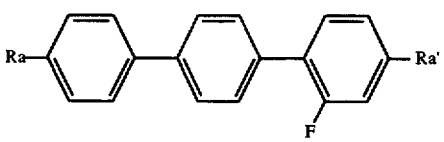 (D47)
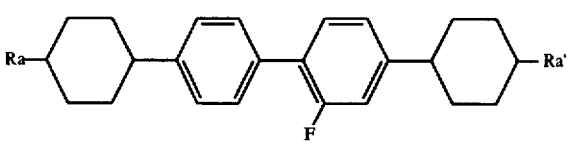 (D48)
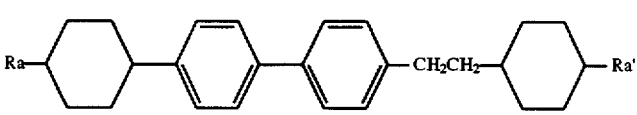 (D49)
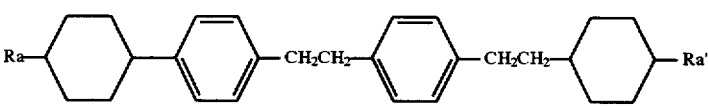 (D50)
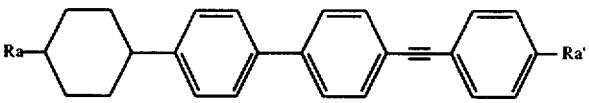 (D51)
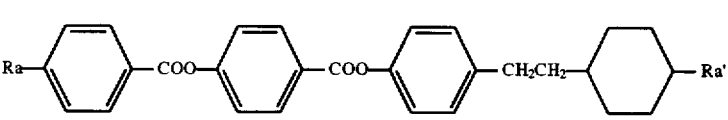

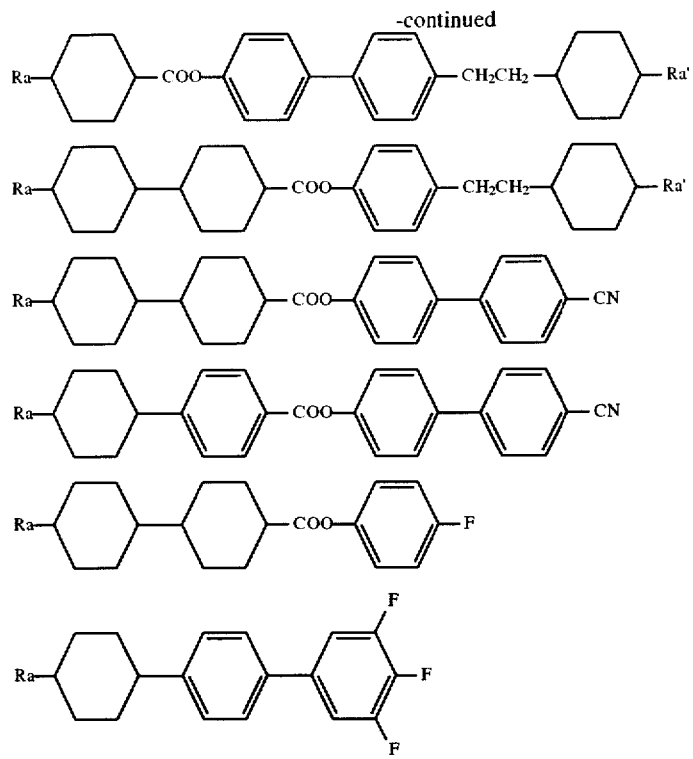
(In the description above, Ra and Ra' show the same meanings as described before.)
The following (E1) to (E18) can be mentioned as the compounds corresponding to (E):
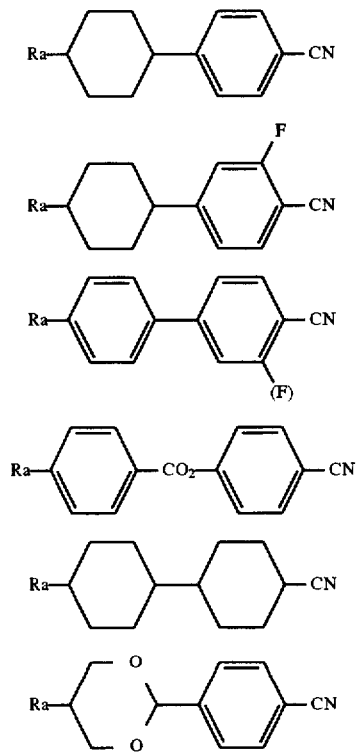
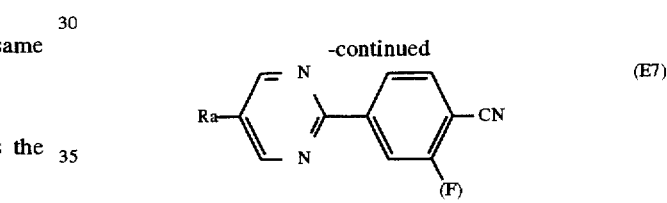

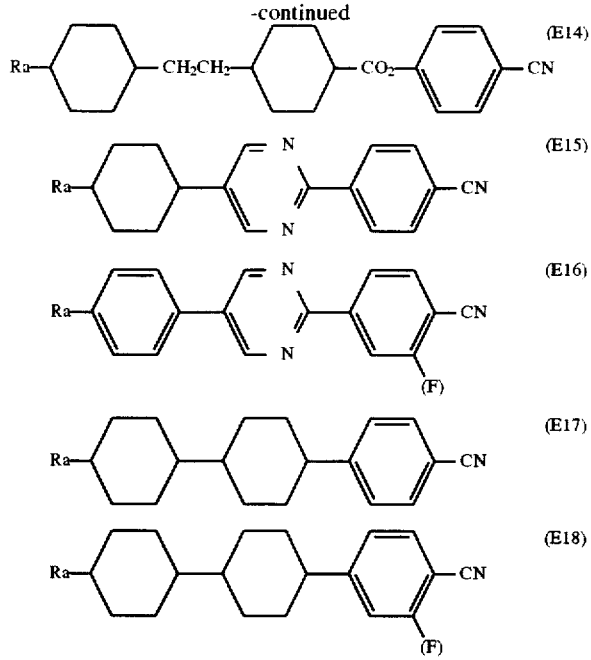

(E14), (E15), (E16), (E17), (E18)

(In the description above, Ra and Ra' show the same meanings as described before.)

Liquid crystal composition of the present invention preferably contains at least one compound expressed by (1) in a ratio of 0.1 to 80% by weight to develop excellent characteristics.

Liquid crystal composition of the present invention has a wide mesomorphic range. Besides, when used for STN or TN liquid crystal display devices, they can achieve improvements in steepness and viewing angle. Also, since the compounds of formula (1) have a low viscosity, liquid crystal display devices using the compounds are improved in their response speed.

The following can be mentioned as examples of the liquid crystal composition of the present invention, particularly as the examples of nematic liquid crystal compositions. In these examples of the composition, No. of the compounds is the same as that shown in the Examples described below:

Example of Composition 1

4-(4-propylcyclohexyl)-(1,1-difluorobutyl)cyclohexane (Compound No. 3) 10%

4-(4-propylcyclohexyl)-(1,1-difluoropentyl)cyclohexane (Compound No. 4) 10%

1,2,3-trifluoro-5-(4-heptylcyclohexyl)benzene 5%

1,2-difluoro-4-(4-(4-ethylcyclohexyl)cyclohexyl)benzene 7%

1,2-difluoro-4-(4-(4-propylcyclohexyl)cyclohexyl) benzene 7%

1,2-difluoro-4-(4-(4-pentylcyclohexyl)cyclohexyl) benzene 7%

1,2,3-trifluoro-5-(4-(2-(4-propylcyclohexyl)ethyl) cyclohexyl)benzene 9%

1,2,3-trifluoro-5-(4-(2-(4-pentylcyclohexyl)ethyl) cyclohexyl)benzene 5%

1,2,3-trifluoro-5-(2-(4-(4-propylcyclohexyl)cyclohexyl) ethyl)benzene 8%

1,2,3-trifluoro-5-(2-(4-(4-pentylcyclohexyl)cyclohexyl) ethyl)benzene 7%

1,2,3-trifluoro-5-(4-(4-propylcyclohexyl)cyclohexyl) benzene 8%

1,2,3-trifluoro-5-(4-(4-pentylcyclohexyl)cyclohexyl) benzene 7%

4-(4-(4-propylcyclohexyl)cyclohexyl)-fluorobenzene 5%

4'-(4-propylcyclohexyl)-4-fluorobiphenyl 5%

The composition mentioned above exhibits the value of physical properties as follows:

Clearing point:80.8° C., Δε:4.7, Δn:0.0689, viscosity:24.9 cP, threshold voltage at a cell thickness of 8.7μ: 2.02 V Example of Composition 2

4-4(propylcyclohexyl)-(2, 2-difluoropentyl)cyclohexane (Compound No. 6) 8%

4-4(propylcyclohexyl)-(3,3-difluoropentyl)cyclohexane (Compound No. 7) 7%

1,2-difluoro-4-(4-heptylcyclohexyl)benzene 5%

1,2-difluoro-4-(2-(4-pentylcyclohexyl)ethyl)benzene 5%

1,2-difluoro-4'-(4-ethylcyclohexyl)biphenyl 5%

1,2-difluoro-4'-(4-propylcyclohexyl)biphenyl 5%

1,2-difluoro-4'-(4-pentylcyclohexyl)biphenyl 10%

1,2-difluoro-4-(4-(2-(4-ethylcyclohexyl)ethyl) cyclohexyl) benzene 10%

1,2-difluoro-4-(4-(2-(4-propylcyclohexyl)ethyl) cyclohexyl) benzene 5%

1,2-difluoro-4-(4-(2-(4-pentylcyclohexyl)ethyl) cyclohexyl) benzene 10%

4-(4-pentylcylcohexyl)-chlorobenzene 5%

4-(4-hexylcyclohexyl)-chlorobenzene 5%

4-(4-(4-propylcyclohexyl)cyclohexyl)-chlorobenzene 5%

4-(4-(4-pentylcyclohexyl)cyclohexyl)-chlorobenzene 5%

1,2,3-trifluoro-5-(4-(4-propylcyclohexyl)cyclohexyl) benzene 5%

1,2,3-trifluoro-5-(4-(4-pentylcyclohexyl)cyclohexyl) benzene 5%

The composition mentioned above exhibits the values of physical properties as follows:

Clearing point:71.5° C., Δε:4.0, Δn:0.0829, viscosity:20.0 cP, threshold voltage at a cell thickness of 8.8μ:2.18 V Example of Composition 3

4-(4-pentylcyclohexyl)-(2, 2-difluorobutyl)cyclohexane (Compound No. 14) 10%

4-(4-pentylcyclohexyl)-(2-fluorobutyl)cyclohexane (Compound No. 60) 10%

1,2-difluoro-4-(2-(4-pentylcyclohexyl)ethyl)benzene 9%

1,2-difluoro-4-(4-(4-ethylcyclohexyl)cyclohexyl)benzene 7%

1,2-difluoro-4-(4-(4-propylcyclohexyl)cyclohexyl) benzene 7%

1,2-difluoro-4-(4-(4-pentylcyclohexyl)cyclohexyl) benzene 7%

1,2-difluoro-4'-(4-ethylcyclohexyl)biphenyl 5%

1,2-difluoro-4'-(4-propylcyclohexyl)biphenyl 5%

1,2-difluoro-4'-(4-pentylcyclohexyl)biphenyl 10%

4-fluorophenyl 4-pentylcyclohexylcarboxylate 7%

4-fluorophenyl 4-heptylcyclohexylcarboxylate 8%

4-(4-(4-propylcyclohexyl)cyclohexyl-methylbenzene 5%

4-(4-(4-propylcyclohexyl)cyclohexyl-propylbenzene 5%

1-chloro-2-fluoro-4-(4-(2-(4-propylcyclohexyl)ethyl) cyclohexyl)benzene 5%

Example of Composition 4

4-(4-(1-butenyl)cyclohexyl)-1-(3-fluoropropyl) cyclohexane (Compound No. 255) 7%

4-(4-(3-butenyl)cyclohexyl)-1-(3-fluoropropyl) cyclohexane (Compound No. 256) 8%

1,2-difluoro-4-(4-(4-ethylcyclohexyl)cyclohexyl)benzene 7%

1,2-difluoro-4-(4-(4-propylcyclohexyl)cyclohexyl) benzene 7%

1,2-difluoro-4-(4-(4-pentylcyclohexyl)cyclohexyl) benzene 7%

4'-(4-ethylcyclohexyl)-3,4-difluorobiphenyl 5%

4'-(4-propylcyclohexyl)-3,4-difluorobiphenyl 5%

4'-(4-pentylcyclohexyl)-3,4-difluorobiphenyl 10%

1,2,3-trifluoro-5-(4-(4-propylcyclohexyl)cyclohexyl) benzene 9%

1,2,3-trifluoro-5-(4-(4-pentylcyclohexyl)cyclohexyl) benzene 5%

4'-(4-propylcyclohexyl)-3,4,5-trifluorobiphenyl 5%

4'-(4-pentylcyclohexyl)-3,4,5-trifluorobiphenyl 5%

1,2,3-trifluoro-5-(4-(2-(4-propylcyclohexyl)ethyl) cyclohexyl)benzene 5%

1,2,3-trifluoro-5-(4-(2-(4-pentylcyclohexyl)ethyl) cyclohexyl)benzene 5%

1,2,3-trifluoro-5-(2-(4-(4-propylcyclohexyl)cyclohexyl) ethyl)benzene 5%

1,2,3-trifluoro-5-(2-(4-(4-pentylcyclohexyl)cyclohexyl) ethyl)benzene 5%

Example of Composition 5

4-(4-propylcyclohexyl)-1-(1,1-difluoropentyloxy) cyclohexane (Compound No. 96) 10%

4-(4-(1-butenyl)cyclohexyl)-1-(3-fluoropentyl) cyclohexane (Compound No. 255) 10%

4-(4-propylcyclohexyl)-chlorobenzene 7%

4-(4-pentylcyclohexyl)-chlorobenzene 7%

4-(4-hexylcyclohexyl)-chlorobenzene 7%

4-(4-(4-ethylcyclohexyl)cyclohexyl)-chlorobenzene 8%

4-(4-(4-propylcyclohexyl)cyclohexyl)-chlorobenzene 8%

4-(4-(4-pentylcyclohexyl)cyclohexyl)-chlorobenzene 8%

1-chloro-2-fluoro-4-(4-(2-(4-ethylcyclohexyl)ethyl) cyclohexyl)benzene 7%

1-chloro-2-fluoro-4-(4-(2-(4-propylcyclohexyl)ethyl) cyclohexyl)benzene 7%

1-chloro-2-fluoro-4-(4-(2-(4-pentylcyclohexyl)ethyl) cyclohexyl)benzene 6%

1,2,3-trifluoro-5-(4-(4-propylcyclohexyl)cyclohexyl) benzene 8%

4'-(4-propylcyclohexyl)-3,4,5-trifluorobiphenyl 7%

Example of Composition 6

4-(4-propylcyclohexyl)-1-(methoxydifluoromethyl) cyclohexane (Compound No. 231) 5%

4-(4-butylcyclohexyl)-1-(2-methoxy-2, 2-difluoroethyl) cyclohexane (Compound No. 235) 5%

4'-ethyl-4-cyanobiphenyl 7%

4'-butyl-4-cyanobiphenyl 8%

4-(4-propylcyclohexyl)-cyanobenzene 10%

4-(4-pentylcyclohexyl)-cyanobenzene 10%

4-(4-methoxymethylcyclohexyl)-propylbenzene 10%

4-(4-methoxymethylcyclohexyl)-pentylbenzene 10%

4-(4-(4-ethylcyclohexyl)cyclohexyl)-methylbenzene 7%

4-(4-(4-propylcyclohexyl)cyclohexyl)-methylbenzene 8%

4-(4-(4-propylcyclohexyl)cyclohexyl)-cyanobenzene 5%

4-(4-(4-propylcyclohexyl)cyclohexyl)-fluorobenzene 5%

4-(4-(4-pentylcyclohexyl)cyclohexyl)-fluorobenzene 5%

4-fluorophenyl-4-(4-propylcyclohexyl)benzoate 5%

Example of Composition 7

4-(4-(3-butenyl)cyclohexyl)-1-(3-fluoropropyl) cyclohexane (Compound No. 256) 8%

4-(4-(2-propenyloxymethyl)cyclohexyl)-1-(3-fluoropropyl) cyclohexane (Compound No. 260) 8%

4-(4-(3-pentenyl)cyclohexyl)-1-(3-fluoropropyl) cyclohexane (Compound No. 257) 9%

2-(3,4-difluorophenyl)-5-propylpyrimidine 5%

2-(3,4-difluorophenyl)-5-pentylpyrimidine 5%

4-(4-ethylcyclohexyl)-cyanobenzene 10%

4-(4-propylcyclohexyl)-cyanobenzene 10%

4-(4-ethylcyclohexyl)-3-fluoro-cyanobenzene 5%

4-(4-propylcyclohexyl)-3-fluoro-cyanobenzene 5%

4-(4-(4-ethylcyclohexyl)cyclohexyl)-cyanobenzene 5%

4-(4-(4-propylcyclohexyl)cyclohexyl)-cyanobenzene 5%

4-(4-(4-ethylcyclohexyl)cyclohexyl)-3-fluoro-cyanobenzene 5%

4-(4-(4-propylcyclohexyl)cyclohexyl)-3-fluoro-cyanobenzene 5%

2-(4'-fluorobiphenyl)-5-propylpyrimidine 5%

2-(4'-fluorobiphenyl)-5-butylpyrimidine 5%

4-(4-propylcyclohexyl)-ethoxybenzene 5%

Example of Composition 8

4-(4-pentylcyclohexyl)-(2-fluorobutyl)cyclohexane (Compound No. 60) 10%

4-(4-propylcyclohexyl)-1-(methoxydifluoromethyl) cyclohexane (Compound No. 231) 10%

4'-ethyl-4-cyanobiphenyl 5%

4-(4-methoxymethylcyclohexyl)-cyanobenzene 5%

4-(4-(2-ethoxyethoxy)cyclohexyl)-cyanobenzene 5%

4-(4-propylcyclohexyl)-cyanobenzene 10%

2-(4-ethylphenyl)-5-ethylpyrimidine 5%

2-(4-ethylphenyl)-5-propylpyrimidine 5%

2-(4-ethylphenyl)-5-butylpyrimidine 5%

2-(4-(4-propylcyclohexyl)phenyl)-5-ethylpyrimidine 5%

2-(4-(4-propylcyclohexyl)phenyl)-5-propylpyrimidine 5%

2-(4-(4-propylcyclohexyl)phenyl)-5-butylpyrimidine 5%

1,2-difluoro-4-(4-(4-ethylcyclohexyl)cyclohexyl)benzene 5%

1,2-difluoro-4-(4-(4-propylcyclohexyl)cyclohexyl) benzene 5%

1,2-difluoro-4-(4-(4-pentylcyclohexyl)cyclohexyl) benzene 5%

4-(4-(4-propylcyclohexyl)cyclohexyl)-methoxybenzene 5%

4-(4-butylcyclohexyl)-propylcyclohexane 5%

Example of Composition 9

4-(4-propylcyclohexyl)-(1,1-difluorobutyl)cyclohexane (Compound No. 3) 10%

4-(4-propylcyclohexyl)-(1,1-difluoropentyl)cyclohexane (Compound No. 4) 10%

4-(4-(3-butenyl)cyclohexyl)-cyanobenzene 7%

4-(4-(3-pentenyl)cyclohexyl)-cyanobenzene 8%

4-(4-propylcyclohexyl)-cyanobenzene 5%

4-(2-(4-ethylphenyl)ethynyl)-methylbenzene 5%

4-(2-(4-methylphenyl)ethynyl)-hexylbenzene 10%

4-(2-(4-butylphenyl)ethynyl)-butylbenzene 5%

4-(2-(2-fluoro-4-(4-propylcyclohexyl)phenyl)ethynyl)-ethylbenzene 5%

4-(2-(2-fluoro-4-(4-propylcyclohexyl)phenyl)ethynyl)-propylbenzene 5%

4-(2-(4-(2-(4-propylcyclohexyl)ethyl)phenyl)ethynyl)-ethylbenzene 5%

4-(2-(4-(2-(4-propylcyclohexyl)ethyl)phenyl)ethynyl)-propylbenzene 5%

2-(4'-fluorobiphenyl)-5-propylpyrimidine 5%

2-(4'-fluorobiphenyl)-5-butylpyrimidine 5%

4-(4-butylcyclohexyl)-propylcyclohexane 5%

4-fluorophenyl-4-(4-propylcyclohexyl)benzoate 5%

The composition mentioned above exhibits the values of physical properties as follows:

Clearing point:77.0° C., $\Delta\epsilon$:4.6, $\Delta$n:0.1637, viscosity:24.0 cP, threshold voltage at a cell thickness of 8.7μ:2.32 V

Example of Composition 10

4-(4-pentylcyclohexyl)-(2,2-difluorobutyl)cyclohexane (Compound No. 14) 10%

4-(4-(2-propenyloxymethyl)cyclohexyl)-1-(3-fluoropropyl) cyclohexane (Compound No. 260) 10%

4-(4-(3-pentenyl)cyclohexyl)-1-(3-fluoropropyl) cyclohexane (Compound No. 257) 10%

2-(4-cyanophenyl)-5-propyldioxane 10%

4-cyanophenyl-4-propyl benzoate 10%

4-fluorophenyl-4-(4-propylcyclohexyl) cyclohexylcarboxylate 5%

4-fluorophenyl-4-(4-pentylcyclohexyl) cyclohexylcarboxylate 5%

4-(2-(4-ethylphenyl)ethynyl)-methoxybenzene 2.5%

4-(2-(4-propylphenyl)ethynyl)-methoxybenzene 2.5%

4-(2-(4-butylphenyl)ethynyl)-ethoxybenzene 2.5%

4-(2-(4-pentylphenyl)ethynyl)-methoxybenzene 2.5%

2-(4-ethoxyphenyl)-5-ethylpyrimidine 5%

2-(4-ethoxyphenyl)-5-propylpyrimidine 5%

4-butoxyphenyl-4-propylcyclohexylcarboxylate 5%

4-etoxycyclohexyl-4-butylcyclohexylcarboxylate 5%

2-fluoro-4- (4-propylcyclohexyl)-cyanobenzene 5%

2-fluoro-4-(4-(4-propylcyclohexyl)cyclohexyl)-cyanobenzene 5%

Example of Composition 11

4-(4-propylcyclohexyl)-(2,2-difluoropentoxy) cyclohexane (Compound No. 98) 8%

4-(4-propylcyclohexyl)-(3,3-difluoropentoxy) cyclohexane (Compound No. 100) 7%

4-(4-propylcyclohexyl)-methoxycyclohexane 7%

4-(4-propylcyclohexyl)-propoxycyclohexane 7%

4-(4-pentylcyclohexyl)-methoxycyclohexane 8%

4-(4-propylcyclohexyl)-fluorobenzene 8%

4-(4-(4-ethylcyclohexyl)cyclohexyl)-trifluoromethoxybenzene 5%

4-(4-(4-propylcyclohexyl)cyclohexyl)-difluoromethoxybenzene 5%

4-(4-(4-propylcyclohexyl)cyclohexyl)-trifluoromethoxybenzene 5%

4-(4-(4-butylcyclohexyl)cyclohexyl)-trifluoromethoxybenzene 5%

4-(4-(4-pentylcyclohexyl)cyclohexyl)-trifluoromethoxybenzene 5%

4-(4-(4-pentylcyclohexyl)cyclohexyl)-difluoromethoxybenzene 5%

2,6-difluoro-4-(4-(4-propylcyclohexyl)cyclohexyl)- difluoromethoxybenzene 5%

2,6-difluoro-4-(4-(4-pentylcyclohexyl)cyclohexyl)- difluoromethoxybenzene 5%

1,2-difluoro-4-(2-(4-(4-propylcyclohexyl)cyclohexyl) ethyl) benzene 5%

1,2-difluoro-4-(2-(4-(4-pentylcyclohexyl)cyclohexyl) ethyl) benzene 5%

3,4-difluoro-4-(4-propylcyclohexyl) cyclohexylcarboxylate 5%

Example of Composition 12

4-(4-(4-propylcyclohexyl)cyclohexyl)-(2,2-difluoropentyl) cyclohexane 10%

4-(4-(4-propylcyclohexyl)cyclohexyl)-(3,3-difluoropentyl) cyclohexane 10%

4-(4-pentylcyclohexyl)-fluorobenzene 7%

4-(4-heptylcyclohexyl)-fluorobenzene 8%

4-(4-(4-ethylcyclohexyl)cyclohexyl)-trifluoromethoxybenzene 7%

4-(4-(4-propylcyclohexyl)cyclohexyl)-trifluoromethoxybenzene 8%

4-(4-(4-butylcyclohexyl)cyclohexyl)-trifluoromethoxybenzene 7%

4-(4-(4-pentylcyclohexyl)cyclohexyl)-trifluoromethoxybenzene 8% 4'-(4-propylcyclohexyl)-1,2-difluorobiphenyl 7%

4'-(4-pentylcyclohexyl)-1,2-difluorobiphenyl 8%

4-(2-(4-(4-propylcyclohexyl)cyclohexyl)ethyl)-trifluoromethoxybenzene 5%

4'-(4-pentylcyclohexyl)-2-fluoro-ethylbenzene 5%

2'-fluoro-4'-(4-propylcyclohexyl)-4-(4-propylcyclohexyl) biphenyl 5%

2'-fluoro-4'-(4-pentylcyclohexyl)-4-(4-propylcyclohexyl) biphenyl 5%

Example of Composition 13

4-(4-(3-butenyloxy)cyclohexyl)-(3-fluoropropyl) cyclohexane (Compound No. 259) 7%

4-(4-(3-butenyl)cyclohexyl)-(2-fluoroethoxy) cyclohexane (Compound No. 217) 8%

4-(4-(2-propenyl)cyclohexyl)-cyanobenzene 3%

4'-butyl-4-ethylbiphenyl 3%

4'-propyl-4-cyanobiphenyl 3%

2-fluoro-4-(4-ethylcyclohexyl)-cyanobenzene 3%

4-(2-(4-propylcyclohexyl)ethyl)-ethoxybenzene 3%
4'-pentyl-4-cyanobiphenyl 5%
4-cyanophenyl-4-propylbenzoate 5%
4-ethylphenyl-4-butylcyclohexylcarboxylate 10%
4-(2-(4-pentylcyclohexyl)ethyl)-ethoxybenzene 10%
4-methoxyphenyl-4-pentylcyclohexylcarboxylate 10%
4-propoxyphenyl-4-pentylcyclohexylcarboxylate 10%
2-(4-cyanophenyl)-5-(4-butylphenyl)pyrimidine 4%
4''-pentyl-4-cyanoterphenyl 4%
4-(2-(4-(4-pentylcyclohexyl)phenyl)ethyl)-butylbenzene 4%
2-(4-pentylphenyl)-5-(4-butylphenyl)pyrimidine 4%
4'-(4-pentylcyclohexyl)-4-(2-(4-propylcyclohexyl)ethyl) biphenyl 4%

Example of Composition 14

4-(4-(3-butenyl)cyclohexyl)-(3-fluoropropyl) cyclohexane (Compound No. 256) 10%
4-(4-(1-(3-propenyloxy)methyl)cyclohexyl)-(3-fluoropropyl) cyclohexane (Compound No. 260) 10%
3,4-difluorophenyl-4-butylcyclohexylcarboxylate 5%
3,4-difluorophenyl-4-pentylcyclohexylcarboxylate 5%
3-fluoro-4-cyanophenyl-4-ethylbenzoate 5%
3-fluoro-4-cyanophenyl-4-propylbenzoate 5%
3-fluoro-4-cyanophenyl-4-butylbenzoate 5%
3-fluoro-4-cyanophenyl-4-pentylbenzoate 5%
2-fluoro-4-(4-(3-methoxypropyl)cyclohexyl)-cyanobenzene 10%
3,4-difluorophenyl-4-(4-propylcyclohexyl) cyclohexylcarboxylate 5%
3,4-difluorophenyl-4-(4-pentylcyclohexyl) cyclohexylcarboxylate 5%
3-fluoro-4-cyanophenyl-4-(4-ethylcyclohexyl)benzoate 5%
3-fluoro-4-cyanophenyl-4-(4-propylcyclohexyl)benzoate 5%
3-fluoro-4-cyanophenyl-4-(4-butylcyclohexyl)benzoate 5%
3-fluoro-4-cyanophenyl-4-(4-pentylcyclohexyl)benzoate 5%
4-(2-(4-(4-propylcyclohexyl)phenyl)ethynyl)-ethylbenzene 10%

Example of Composition 15

4-(4-pentylcyclohexyl)-(2,2-difluorobutyl)cyclohexane (Compound No. 14) 10%
4-(4-propylcyclohexyl)-(2-fluoropentyl)cyclohexane (Compound No. 52) 10%
1,2-difluoro-4-(2-(4-pentylcyclohexyl)ethyl)benzene 9%
1,2-difluoro-4-(4-(4-ethylcyclohexyl)cyclohexyl)benzene 7%
1,2-difluoro-4-(4-(4-propylcyclohexyl)cyclohexyl)benzene 7%
1,2-difluoro-4-(4-(4-pentylcyclohexyl)cyclohexyl)benzene 7%
1,2-difluoro-4'-(4-ethylcyclohexyl)biphenyl 5%
1,2-difluoro-4'-(4-propylcyclohexyl)biphenyl 5%
1,2-difluoro-4'-(4-pentylcyclohexyl)biphenyl 10%
4-fluorophenyl-4-pentylcyclohexylcarboxylate 7%
4-fluorophenyl-4-heptylcyclohexylcarboxylate 8%
4-(4-(4-propylcyclohexyl)cyclohexyl)-methylbenzene 5%
4-(4-(4-propylcyclohexyl)cyclohexyl)-propylbenzene 5%
1-chloro-2-fluoro-4-(4-(2-(4-propylcyclohexyl)ethyl) cyclohexyl)benzene 5%

The composition mentioned above exhibits the values of physical properties as follows:

Clearing point:75.8° C., Δε:2.9, Δn:0.0815, viscosity:19.1 cP, threshold voltage at a cell thickness of 8.8μ:2.49 V

Example of Composition 16

4-(4-propylcyclohexyl)-1-(1,1-difluoroethyl)cyclohexane (Compound No. 1) 10%
4-(4-propylcyclohexyl)-1-(1,1-difluoropropyl) cyclohexane (Compound No. 2) 10%
4-(4-propylcyclohexyl)-chlorobenzene 7%
4-(4-pentylcyclohexyl)-chlorobenzene 7%
4-(4-hexylcyclohexyl)-chlorobenzene 7%
4-(4-(4-ethylcyclohexyl)cyclohexyl)-chlorobenzene 8%
4-(4-(4-propylcyclohexyl)cyclohexyl)-chlorobenzene 8%
4-(4-(4-pentylcyclohexyl)cyclohexyl)-chlorobenzene 8%
1-chloro-2-fluoro-4-(4-(2-(4-ethylcyclohexyl)ethyl) cyclohexyl)benzene 7%
1-chloro-2-fluoro-4-(4-(2-(4-propylcyclohexyl)ethyl) cyclohexyl)benzene 7%
1-chloro-2-fluoro-4-(4-(2-(4-pentylcyclohexyl)ethyl) cyclohexyl)benzene 6%
1,2,3-trifluoro-5-(4-(4-propylcyclohexyl)cyclohexyl) benzene 8%
4'-(4-propylcyclohexyl)-3,4,5-trifluorobiphenyl 7%

The composition mentioned above exhibits the values of physical properties as follows:

Clearing point:78.2° C., Δε:3.7, Δn:0.0883, viscosity:20.9 cP, threshold voltage at a cell thickness of 8.7μ:2.41 V

Example of Composition 17

4-(4-pentylcyclohexyl)-1-(2-fluoroethyloxy)cyclohexane (Compound No. 215) 5%
4-(2-(4-pentylcyclohexyl)ethyl)-1(2-fluoroethyloxy) cyclohexane (Compound No. 226) 5%
4'-ethyl-4-cyanobiphenyl 7%
4'-butyl-4-cyanobiphenyl 8%
4-(4-propylcyclohexyl)-cyanobenzene 10%
4-(4-pentylcyclohexyl)-cyanobenzene 10%
4-(4-methoxymethylcyclohexyl)-propylbenzene 10%
4-(4-methoxymethylcyclohexyl)-pentylbenzene 10%
4-(4-(4-ethylcyclohexyl)cyclohexyl)-methylbenzene 7%
4-(4-(4-propylcyclohexyl)cyclohexyl)-methylbenzene 8%
4-(4-(4-propylcyclohexyl)cyclohexyl)-cyanobenzene 5%
4-(4-(4-propylcyclohexyl)cyclohexyl)-fluorobenzene 5%
4-(4-(4-pentylcyclohexyl)cyclohexyl)-fluorobenzene 5%
4-fluorophenyl-4-(4-propylcyclohexyl)benzoate 5%

The composition mentioned above exhibits the values of physical properties as follows:

Clearing point:79.7° C., Δε:6.5, Δn:0.1120, viscosity:19.2 cP, threshold voltage at a cell thickness of 8.8μ: 2.02 V

Example of Composition 18

4-(4-(1-pentenyl)cyclohexyl)-1-(2-fluoroethyl) cyclohexane (Compound No. 252) 10%

4-(4-(3-butenyl)cyclohexyl)-1-cyanobenzene 7%

4-(4-(3-pentenyl)cyclohexyl)-1-cyanobenzene 7%

4-(4-propylcyclohexyl)-1-cyanobenzene 16%

4-(4-propylcyclohexyl)-1-fluorobenzene 4%

4-(4-propylcyclohexyl)-1-ethyloxybenzene 9%

4-(2-(4-ethylphenyl)ethynyl)-1-methyloxybenzene 5%

4-(4-(4-propylcyclohexyl)cyclohexyl)-1-methylbenzene 7%

4-(4-(4-propylcyclohexyl)cyclohexyl)-1-methyloxybenzene 4%

4-(2-(2-fluoro-4-(4-propylcyclohexyl)phenyl)ethynyl)-1-ethylbenzene 5%

4-(2-(2-fluoro-4-(4-propylcyclohexyl)phenyl)ethynyl)-1-propylbenzene 5%

4-(2-(2-fluoro-4-(4-propylcyclohexyl)phenyl)ethynyl)-1-butylbenzene 5%

4-(4-(4-ethylcyclohexyl)cyclohexyl)-1-cyanobenzene 5%

4-(4-(4-propylcyclohexyl)cyclohexyl)-1-cyanobenzene 5%

2-(4-(4-propylcyclohexyl)phenyl)-5-ethylpyrimidine 3%

2-(4-(4-propylcyclohexyl)phenyl)-5-propylpyrimidine 3%

The composition mentioned above exhibits the values of physical properties as follows:

Clearing point:99.5° C., Δε:7.0, Δn:0.1461, Viscosity:21.0 cP, Threshold voltage at a cell thickness of 8.7μ:2.24 V The present invention will be explained below in more detail with reference to Examples. In the following Examples, all of the cyclohexane rings and double bonds in compounds belong to trans-form. Cr represents crystal, SB does smectic B phase, SX does unidentified smectic phase, and Iso represents isotropic liquid, and all phase transition points are 1° C.

EXAMPLE 1

Production of 4-(4-pentylcyclohexyl)-(2,2-difluorobutyl) cyclohexane (Compound expressed by the fourmula (1) wherein $R_1$ is $C_5H_{11}$, X is F, Y is H, Q and m are 0, n is 1, p is 2. (Compound No. 14))

First stage

A mixture of 50 g (0.17 mol) of 4-(4-pentylcyclohexyl) cyclohexyl acetic acid and 135 Ml of thionyl chloride was heated for 4 hours to reflux. Excess amount of thionyl chloride was separated under a reduced pressure to obtain 4-(4-pentylcyclohexyl)cyclohexyl acetic acid chloride.

On the other hand, a solution of 27.8 g (0.26 mol) of ethyl bromide in 50 ml of THF was added dropwise to a mixture of 6.2 g (0.26 mol) of magnesium and 10 Ml of THF at a temperature of lower than 20° C. and then stirred for 2 hours at a room temperature to obtain a THF solution of ethylmagnesium bromide.

Dried toluene in an amount of 650 ml and 4.5 g (5% by weight of acid chloride) of Fe(acac)$_3$ were added to the 4-(4-pentylcyclohexyl)cyclohexyl acetic acid chloride obtained in a previous procedure and cooled down to -30° C. This solution was added dropwise with the whole amount of the solution of ethyl magnesium bromide obtained in a previous procedure at a temperature of lower than -30° C. and then stirred for 15 min at the same temperature. The reaction product was put in 500 ml of 6N hydrochloric acid and then extracted with 150 ml of toluene. The organic layer was washed with 6 N hydrochloric acid once, with 2N aqueous solution of sodium hydroxide thrice, and with water twice, and then dried over anhydrous magnesium sulfate. After the magnesium sulfate was separated, the solvent was distilled off under a reduced pressure, and the residue thus obtained was subjected to a silica gel column chromatography (eluate: toluene) to obtain 39.8 g of a crude 4-(4-pentylcyclohexyl)-(2-oxyobutyl)cyclohexane. This product was recrystallized from 50 ml of ethanol to obtain 32.1 g (yield 62%) of 4-(4-pentylcyclohexyl)-(2-oxobutyl) cyclohexane. Melting point: 107.3°-107.4° C.

Second stage

A mixture of 10 g (33 mmol) of 4-(4-pentylcyclohexyl)-(2-oxobutyl) cyclohexane obtained in the first stage, 10.5 g (65 mmol) of DAST, and 100 ml of THF was heated for 90 hours to reflux. The reaction product was put in 100 ml of an ice water and then extracted with 100 ml of toluene. The organic layer was washed with an aqueous solution saturated with potassium carbonate once and with a salt water thrice, and dried over anhydrous magnesium sulfate. After the magnesium sulfate was separated, the solvent was distilled off under a reduced pressure, and the residue thus obtained was subjected to a silica gel column chromatography (eluate: heptane) to obtain 1.58 g of a crude 4-(4-pentylcyclohexyl)-(2,2-difluorobutyl) cyclohexane. This product was recrystallized from 30 ml of ethanol in a freezer to obtain 1.02 g (yield 10%) of 4-(4-pentylcyclohexyl)-(2,2-difluorobutyl)cyclohexane. Several kinds of spectra well supported its structure.

$^1$H-NMR (TMS internal standard) δ (ppm): 0.69–2.06 (m)

GC-MS: 328 (M+)

Cr 2.3 SB 115.4 Iso (Unit is °C. The same is applied hereinafter.)

While the clearing point of the compound of the present invention was 115.4° C. as mentioned above, it can be understood that the value is higher compared with the clearing point of 104° C. of the known bicyclohexane type compounds having the same structure except that the alkyl group at the end of molecule is not substituted with a fluorine atom (reference is made to Examined Japanese Patent Publication No. 5-020418).

The following compounds (No. 1 through No. 46) were produced according to the method in Example 1. Each of the compounds are indicated by excerpting parameters $R_1$, Q, and —(CH$_2$)$_n$CF$_2$(CH$_2$)pH in the compounds expressed by the general formula (1) (in the case of m=0, X=F, and Y=H in the group —(O)$_m$—(CH$_2$)$_n$—CFX—(CH$_2$)$_p$—Y of the general formula (1)).

| Compound No. | $R_1$ | l | —(CH$_2$)nCF$_2$(CH$_2$)pH | Phase transition point |
|---|---|---|---|---|
| 1 | $C_3H_7$ | 0 | —CF$_2$CH$_3$ | Cr 5.1 SX 68.9 SB 77.1 Iso |
| 2 | $C_3H_7$ | 0 | —CH$_2$CF$_2$CH$_3$ | Cr 23.0 SB 91.4 Iso |
| 3 | $C_3H_7$ | 0 | —CF$_2$(CH$_2$)$_3$H | Cr 21.9 SB 8.8 Iso |
| 4 | $C_3H_7$ | 0 | —CF$_2$(CH$_2$)$_4$H | Cr 35.3 SB 89.6 |

-continued

| Compound No. | $R_1$ | I | $-(CH_2)nCF_2(CH_2)pH$ | Phase transition point |
|---|---|---|---|---|
| 5 | $C_3H_7$ | 0 | $-CH_2CF_2(CH_2)_2H$ | Iso |
| 6 | $C_3H_7$ | 0 | $-CH_2CF_2(CH_2)_3H$ | Cr 22.1 SB 105.9 Iso |
| 7 | $C_3H_7$ | 0 | $-(CH_2)_2CF_2(CH_2)_2H$ | Cr 17.5 SB 114.4 Iso |
| 8 | $C_3H_7$ | 0 | $-(CH_2)_3CF_2(CH_2)_2H$ | |
| 9 | $C_3H_7$ | 0 | $-(CH_2)_3CF_2CH_3$ | |
| 10 | $C_4H_9$ | 0 | $-CF_2(CH_2)_4H$ | |
| 11 | $C_4H_9$ | 0 | $-(CH_2)_3CF_2CH_3$ | |
| 12 | $C_5H_{11}$ | 0 | $-CF_2(CH_2)_3H$ | |
| 13 | $C_5H_{11}$ | 0 | $-CF_2(CH_2)_4H$ | |
| 14 | $C_5H_{11}$ | 0 | $-CH_2CF_2(CH_2)_2H$ | Cr 2.3 SB 115.4 Iso |
| 15 | $C_5H_{11}$ | 0 | $-CH_2CF_2(CH_2)_3H$ | |
| 16 | $C_5H_{11}$ | 0 | $-(CH_2)_2CF_2CH_3$ | |
| 17 | $C_5H_{11}$ | 0 | $-(CH_2)_2CF_2(CH_2)_2H$ | |
| 18 | $C_5H_{11}$ | 0 | $-(CH_2)_3CF_2CH_3$ | |
| 19 | $C_6H_{13}$ | 0 | $-CF_2(CH_2)_4H$ | |
| 20 | $C_6H_{13}$ | 0 | $-(CH_2)_3CF_2CH_3$ | |
| 21 | $C_3H_7CH=CH-$ | 0 | $-CH_2CF_2(CH_2)_2H$ | |
| 22 | $CH_3CH=CH(CH_2)_2-$ | 0 | $-CH_2CF_2(CH_2)_2H$ | |
| 23 | $CH_2=CHCH_2OCH_2-$ | 0 | $-CH_2CF_2(CH_2)_2H$ | |
| 24 | $C_2H_5$ | 1 | $-CF_2(CH_2)_2H$ | |
| 25 | $C_2H_5$ | 1 | $-CH_2CF_2(CH_2)_2H$ | |
| 26 | $C_3H_7$ | 1 | $-CF_2(CH_2)_3H$ | |
| 27 | $C_3H_7$ | 1 | $-CF_2(CH_2)_4H$ | |
| 28 | $C_3H_7$ | 1 | $-CH_2CF_2(CH_2)_2H$ | |
| 29 | $C_3H_7$ | 1 | $-CH_2CF_2(CH_2)_3H$ | |
| 30 | $C_3H_7$ | 1 | $-(CH_2)_2CF_2CH_3$ | |
| 31 | $C_3H_7$ | 1 | $-(CH_2)_3CF_2(CH_2)_2H$ | |
| 32 | $C_3H_7$ | 1 | $-(CH_2)_3CF_2CH_3$ | |
| 33 | $C_4H_9$ | 1 | $-CF_2(CH_2)_4H$ | |
| 34 | $C_4H_9$ | 1 | $-(CH_2)_3CF_2CH_3$ | |
| 35 | $C_5H_{11}$ | 1 | $-CF_2(CH_2)_2H$ | Cr27.5 SB89.2 Iso |
| 36 | $C_5H_{11}$ | 1 | $-CF_2(CH_2)_4H$ | |
| 37 | $C_5H_{11}$ | 1 | $-CH_2CF_2(CH_2)_2H$ | |
| 38 | $C_5H_{11}$ | 1 | $-CH_2CF_2(CH_2)_3H$ | |
| 39 | $C_5H_{11}$ | 1 | $-(CH_2)_2CF_2CH_3$ | |
| 40 | $C_5H_{11}$ | 1 | $-(CH_2)_3CF_2(CH_2)_2H$ | |
| 41 | $C_5H_{11}$ | 1 | $-(CH_2)_3CF_2CH_3$ | |
| 42 | $C_6H_{13}$ | 1 | $-CF_2(CH_2)_4H$ | |
| 43 | $C_6H_{13}$ | 1 | $-(CH_2)_3CF_2CH_3$ | |
| 44 | $C_7H_{15}$ | 1 | $-CH_2CF_2(CH_2)_2H$ | |
| 45 | $C_8H_{17}$ | 1 | $-CH_2CF_2(CH_2)_2H$ | |
| 46 | $C_9H_{19}$ | 1 | $-CH_2CF_2(CH_2)_2H$ | |

EXAMPLE 2

Production of 4-(4-pentylcyclohexyl)-(2-fluorobutyl) cyclohexane (Compound expressed by the formula (1) wherein $R_1$ is $C_5H_{11}$, X and Y are H, Q and m are 0, n is 1, and p is 2. (Compound No. 60))

First Stage

While keeping inside of a reaction system at a temperature of lower than 10° C., a solution of 5.0 g (16.3 mmol) of 4-(4-pentylcyclohexyl)-(oxobutyl)cyclohexane obtained in Example 1 and dissolved in 35 ml of THF was added dropwise to a mixture of 0.46 g (12.2 mmol) of LAH and 2.5 ml of THF and further stirred for 5 hours at a room temperature. Under cooled condition, 5 ml of ethyl acetate and then 100 ml of 6N hydrochloric acid were added to terminate the reaction. After extracted with 50 ml of ethyl acetate, the organic layer was washed with water twice and dried over anhydrous magnesium sulfate. After the magnesium sulfate was separated, the solvent was distilled off under a reduced pressure, and the residue thus obtained was recrystallized from 8 ml of hexane to obtain 5.0 g (yield 99%) of 4-(4-pentylcyclohexyl)-(2-hydroxybutyl) cyclohexane. Melting point: 130.9°–131.1° C.

Second stage

A mixture of 3.32 g (10.8 mmol) of 4-(4-pentylcyclohexyl)-(2-hydorxybutyl)cyclohexane obtained in the first stage, 2.6 g (16.2 mmol) of DAST, and 30 ml of dichloromethane was stirred for 2 hours at a temperature of lower than 10° C. The reaction product was put in 50 ml of an ice water and then extracted with 50 ml of toluene. The organic layer was washed with an aqueous solution saturated with sodium hydrogencarbonate once and with water twice, and dried over anhydrous magnesium sulfate. After the magnesium sulfate was separated, the solvent was distilled off under a reduced pressure, and the residue thus obtained was subjected to a silica gel column chromatography (eluate: heptane) to obtain 1.3 g of a crude 4-(4-pentylcyclohexyl)-(2-fluorobutyl)cyclohexane. This product was recrystallized twice from a mixed solvent of 8 nQ of ethanol and 2 ml of benzene in a freezer to obtain 0.81 g (yield 24%) of 4-(4-pentylcyclohexyl)-(2-fluorobutyl) cyclohexane. Several kinds of spectra well supported its structure.

$^1$H-NMR (TMS internal standard) δ (ppm): 4.51 (dm, 1H), 1.83–0.81 (m, 38H)

GC-MS: 310 (M+)

Cr 10.4 SB 119.9 Iso

It can be understood that the clearing point 119.9° C. mentioned above is considerably higher compared with the clearing point of 104° C. of the known bicyclohexane type compound having the same structure except that the alkyl group at the end of molecule is not substituted with a fluorine atom (reference is made to Examined Japanese Patent Publication No. 5-020418).

The following compounds (No. 47 through No. 92) were produced according to the method in Example 2. Each of the compounds are indicated by excerpting parameters $R_1$, Q, and $-(CH_2)_nCFH(CH_2)_pH$ in the same way as described before.

| Compound No. | $R_1$ | I | $-(CH_2)nCFH(CH_2)pH$ | Phase transition point |
|---|---|---|---|---|
| 47 | $C_2H_5$ | 0 | $-CFH(CH_2)_2H$ | |
| 48 | $C_2H_5$ | 0 | $-CH_2CFH(CH_2)_2H$ | |
| 49 | $C_3H_7$ | 0 | $-CFH(CH_2)_3H$ | |
| 50 | $C_3H_7$ | 0 | $-CFH(CH_2)_4H$ | |
| 51 | $C_3H_7$ | 0 | $-CH_2CFH(CH_2)_2H$ | |
| 52 | $C_3H_7$ | 0 | $-CH_2CFH(CH_2)_3H$ | Cr 41.5 SB 110.2 Iso |
| 53 | $C_3H_7$ | 0 | $-(CH_2)_2CFHCH_3$ | Cr 33.5 SB 107.1 Iso |
| 54 | $C_3H_7$ | 0 | $-(CH_2)_3CFH(CH_2)_2H$ | |
| 55 | $C_3H_7$ | 0 | $-(CH_2)_3CFHCH_3$ | |
| 56 | $C_4H_9$ | 0 | $-CFH(CH_2)_4H$ | |
| 57 | $C_4H_9$ | 0 | $-(CH_2)_3CFHCH_3$ | |
| 58 | $C_5H_{11}$ | 0 | $-CFH(CH_2)_3H$ | |

-continued

| Compound No. | $R_1$ | I | —(CH$_2$)mCFH(CH$_2$)pH | Phase transition point |
|---|---|---|---|---|
| 59 | $C_5H_{11}$ | 0 | —CFH(CH$_2$)$_4$H | |
| 60 | $C_5H_{11}$ | 0 | —CH$_2$CFH(CH$_2$)$_2$H | Cr 10.4 SB 119.9 Iso |
| 61 | $C_5H_{11}$ | 0 | —CH$_2$CFH(CH$_2$)$_3$H | |
| 62 | $C_5H_{11}$ | 0 | —(CH$_2$)$_2$CFHCH$_3$ | |
| 63 | $C_5H_{11}$ | 0 | —(CH$_2$)$_3$CFH(CH$_2$)$_2$H | |
| 64 | $C_5H_{11}$ | 0 | —(CH$_2$)$_3$CFHCH$_3$ | |
| 65 | $C_6H_{13}$ | 0 | —CFH(CH$_2$)$_4$H | |
| 66 | $C_6H_{13}$ | 0 | —(CH$_2$)$_3$CFHCH$_3$ | |
| 67 | $C_3H_7$CH=CH— | 0 | —CH$_2$CFH(CH$_2$)$_2$H | |
| 68 | $CH_3$CH=CH(CH$_2$)$_2$— | 0 | —CH$_2$CFH(CH$_2$)$_2$H | |
| 69 | $CH_2$=CHCH$_2$OCH$_2$— | 0 | —CH$_2$CFH(CH$_2$)$_2$H | |
| 70 | $C_2H_5$ | 1 | —CFH(CH$_2$)$_2$H | |
| 71 | $C_2H_5$ | 1 | —CH$_2$CFH(CH$_2$)$_2$H | |
| 72 | $C_3H_7$ | 1 | —CFH(CH$_2$)$_3$H | |
| 73 | $C_3H_7$ | 1 | —CFH(CH$_2$)$_4$H | |
| 74 | $C_3H_7$ | 1 | —CH$_2$CFH(CH$_2$)$_2$H | |
| 75 | $C_3H_7$ | 1 | —CH$_2$CFH(CH$_2$)$_3$H | |
| 76 | $C_3H_7$ | 1 | —(CH$_2$)$_2$CFHCH$_3$ | |
| 77 | $C_3H_7$ | 1 | —(CH$_2$)$_3$CFH(CH$_2$)$_2$H | |
| 78 | $C_3H_7$ | 1 | —(CH$_2$)$_3$CFHCH$_3$ | |
| 79 | $C_4H_9$ | 1 | —CFH(CH$_2$)$_4$H | |
| 80 | $C_4H_9$ | 1 | —(CH$_2$)$_3$CFHCH$_3$ | |
| 81 | $C_5H_{11}$ | 1 | —CFH(CH$_2$)$_3$H | |
| 82 | $C_5H_{11}$ | 1 | —CFH(CH$_2$)$_4$H | |
| 83 | $C_5H_{11}$ | 1 | —CH$_2$CFH(CH$_2$)$_2$H | |
| 84 | $C_5H_{11}$ | 1 | —CH$_2$CFH(CH$_2$)$_3$H | |
| 85 | $C_5H_{11}$ | 1 | —(CH$_2$)$_2$CFHCH$_3$ | |
| 86 | $C_5H_{11}$ | 1 | —(CH$_2$)$_3$CFH(CH$_2$)$_2$H | |
| 87 | $C_5H_{11}$ | 1 | —(CH$_2$)$_3$CFHCH$_3$ | |
| 88 | $C_6H_{13}$ | 1 | —CFH(CH$_2$)$_4$H | |
| 89 | $C_6H_{13}$ | 1 | —(CH$_2$)$_3$CFHCH$_3$ | |
| 90 | $C_7H_{15}$ | 1 | —CH$_2$CFH(CH$_2$)$_2$H | |
| 91 | $C_8H_{17}$ | 1 | —CH$_2$CFH(CH$_2$)$_2$H | |
| 92 | $C_9H_{19}$ | 1 | —CH$_2$CFH(CH$_2$)$_2$H | |

EXAMPLE 3

Production of 4-(4-pentylcyclohexyl)-(2,2-difluorobutyloxy) cyclohexane (Compound expressed by the formula (1) wherein $R_1$ is $C_5H_{11}$, X is F, Y is H, Q is O, m and n are 1, and p is 2. (Compound No. 106))

First Stage

A solution of 25.2 g (0.1 mol) of 4-(4-pentylcyclohexyl) cyclohexanol in 50 ml of THF was added dropwise to a mixture of 5.2 g (0.11 mol) of sodium hydride and 20 ml of THF at a temperature of lower than 10° C. Then, 50 ml of DMF was further added and stirred for 1 hour at a room temperature. While keeping inside of the reaction system at a temperature of lower than 0°C., a solution of 21 g (0.1 mol) of 2-bromomethyl-2-ethyl-1,3-dioxane derived from commercially available 1-bromo-2-butanone in 50 ml of THF was added dropwise, and stirred for 2 hours at a room temperature and then for 2 hours at 50° C. This solution was added with 50 ml of 6N hydrochloric acid, stirred for 1 hour at 50° C., added with 200 ml of toluene, and extracted. The organic layer was washed once with an aqueous solution saturated with potassium carbonate and twice with water, and dried over anhydrous magnesium sulfate. After the anhydrous magnesium sulfate was separated, the solvent was distilled off under a reduced pressure, and the residue thus obtained was subjected to a silica gel column chromatography (eluate: toluene) to obtain 20.9 g (yield 65%) of 4-(4-pentylcyclohexyl)-(2-oxobutyloxy)cyclohexane.

Second stage

A mixture of 9.7 g (0.03 mol) of 4-(4-pentylcyclohexyl)-(2-orxobutyloxy)cyclohexane obtained in the first stage, 9.7 g (0.06 mol) of DAST, and 100 ml of THF was heated for 80 hours to reflux. The reaction product was put in 100 ml of an ice water and then extracted with 100 ml of toluene. The organic layer was washed with an aqueous solution saturated with potassium carbonate once and with a salt water five times, and dried over anhydrous magnesium sulfate. After the magnesium sulfate was separated, the solvent was distilled off under a reduced pressure, and the residue thus obtained was subjected to a silica gel column chromatography (eluate: heptane), and recrystallized from 45 ml of ethanol in a freezer to obtain 1.65 g (yield 16%) of 4-(4-pentylcyclohexyl)-(2,2-difluorobutyloxy) cyclohexane. Several kinds of spectra well supported its structure.

The following compounds (No. 93 through No. 138) were produced according to the method in Example 3. Each of the compounds are indicated by excerpting parameters $R_1$, Q, and —O(CH$_2$)$_n$CF$_2$(CH$_2$)$_p$H in the same way as described before.

| Compound No. | $R_1$ | I | —O(CH$_2$)mCF$_2$(CH$_2$)pH |
|---|---|---|---|
| 93 | $C_2H_5$ | 0 | —OCF$_2$(CH$_2$)$_2$H |
| 94 | $C_2H_5$ | 0 | —OCH$_2$CF$_2$(CH$_2$)$_2$H |
| 95 | $C_3H_7$ | 0 | —OCF$_2$(CH$_2$)$_3$H |
| 96 | $C_3H_7$ | 0 | —OCF$_2$(CH$_2$)$_4$H |
| 97 | $C_3H_7$ | 0 | —OCH$_2$CF$_2$(CH$_2$)$_2$H |
| 98 | $C_3H_7$ | 0 | —OCH$_2$CF$_2$(CH$_2$)$_3$H |
| 99 | $C_3H_7$ | 0 | —O(CH$_2$)$_2$CF$_2$CH$_3$ |
| 100 | $C_3H_7$ | 0 | —O(CH$_2$)$_2$CF$_2$(CH$_2$)$_2$H |
| 101 | $C_3H_7$ | 0 | —O(CH$_2$)$_3$CF$_2$CH$_3$ |
| 102 | $C_4H_9$ | 0 | —OCF$_2$(CH$_2$)$_4$H |
| 103 | $C_4H_9$ | 0 | —O(CH$_2$)$_3$CF$_2$CH$_3$ |
| 104 | $C_5H_{11}$ | 0 | —OCF$_2$(CH$_2$)$_3$H |
| 105 | $C_5H_{11}$ | 0 | —OCF$_2$(CH$_2$)$_4$H |
| 106 | $C_5H_{11}$ | 0 | —OCH$_2$CF$_2$(CH$_2$)$_2$H |
| 107 | $C_5H_{11}$ | 0 | —OCH$_2$CF$_2$(CH$_2$)$_3$H |
| 108 | $C_5H_{11}$ | 0 | —O(CH$_2$)$_2$CF$_2$CH$_3$ |
| 109 | $C_5H_{11}$ | 0 | —O(CH$_2$)$_3$CF$_2$(CH$_2$)$_2$H |
| 110 | $C_5H_{11}$ | 0 | —O(CH$_2$)$_3$CF$_2$CH$_3$ |
| 111 | $C_6H_{13}$ | 0 | —OCF$_2$(CH$_2$)$_4$H |
| 112 | $C_6H_{13}$ | 0 | —O(CH$_2$)$_3$CF$_2$CH$_3$ |
| 113 | $C_3H_7$CH=CH— | 0 | —OCF$_2$(CH$_2$)$_2$H |
| 114 | $C_3H_7$CH=CH— | 0 | —OCH$_2$CF$_2$(CH$_2$)$_2$H |
| 115 | $CH_2$=CHCH$_2$OCH$_2$— | 0 | —OCF$_2$(CH$_2$)$_2$H |
| 116 | $C_2H_5$ | 1 | —OCF$_2$(CH$_2$)$_2$H |
| 117 | $C_2H_5$ | 1 | —OCH$_2$CF$_2$(CH$_2$)$_2$H |
| 118 | $C_3H_7$ | 1 | —OCF$_2$(CH$_2$)$_3$H |
| 119 | $C_3H_7$ | 1 | —OCF$_2$(CH$_2$)$_4$H |
| 120 | $C_3H_7$ | 1 | —OCH$_2$CF$_2$(CH$_2$)$_2$H |
| 121 | $C_3H_7$ | 1 | —OCH$_2$CF$_2$(CH$_2$)$_3$H |
| 122 | $C_3H_7$ | 1 | —O(CH$_2$)$_2$CF$_2$CH$_3$ |
| 123 | $C_3H_7$ | 1 | —O(CH$_2$)$_3$CF$_2$(CH$_2$)$_2$H |
| 124 | $C_3H_7$ | 1 | —O(CH$_2$)$_3$CF$_2$CH$_3$ |
| 125 | $C_4H_9$ | 1 | —OCF$_2$(CH$_2$)$_4$H |
| 126 | $C_4H_9$ | 1 | —O(CH$_2$)$_3$CF$_2$CH$_3$ |
| 127 | $C_5H_{11}$ | 1 | —OCF$_2$(CH$_2$)$_3$H |
| 128 | $C_5H_{11}$ | 1 | —OCF$_2$(CH$_2$)$_4$H |
| 129 | $C_5H_{11}$ | 1 | —OCH$_2$CF$_2$(CH$_2$)$_2$H |
| 130 | $C_5H_{11}$ | 1 | —OCH$_2$CF$_2$(CH$_2$)$_3$H |
| 131 | $C_5H_{11}$ | 1 | —O(CH$_2$)$_2$CF$_2$CH$_3$ |
| 132 | $C_5H_{11}$ | 1 | —O(CH$_2$)$_3$CF$_2$(CH$_2$)$_2$H |
| 133 | $C_5H_{11}$ | 1 | —O(CH$_2$)$_3$CF$_2$CH$_3$ |
| 134 | $C_6H_{13}$ | 1 | —OCF$_2$(CH$_2$)$_4$H |
| 135 | $C_6H_{13}$ | 1 | —O(CH$_2$)$_3$CF$_2$CH$_3$ |
| 136 | $C_7H_{15}$ | 1 | —OCH$_2$CF$_2$(CH$_2$)$_2$H |
| 137 | $C_8H_{17}$ | 1 | —OCH$_2$CF$_2$(CH$_2$)$_2$H |
| 138 | $C_9H_{19}$ | 1 | —OCH$_2$CF$_2$(CH$_2$)$_2$H |

EXAMPLE 4

Production of 4-(4-propylcyclohexyl)-(3,3-difluoropropyloxy)cyclohexane (Compound expressed by the formula (1) wherein $R_1$ is $C_3H_7$, X is F, Y is H, Q is O, m is 1, n is 2, and p is 0.(Compound No. 141))

First Stage

A mixture of 94.3 g (0.42 mol) of 4-(4-propylcyclohexyl) cyclohexanone, 64.5 g (0.85 mol) of 1,3-propanediol, 2 ml of concentrated hydrochloric acid, and 200 ml of toluene was heated while stirring to reflux for 3 hours while separating produced water by Dean and Stark method. The product was put in 500 ml of an aqueous solution saturated with sodium hydrogencarbonate, and the organic layer separated was washed with water twice and dried over anhydrous magnesium sulfate. After the magnesium sulfate was separated, the solvent was distilled off under a reduced pressure and the residue was recrystallized from 100 ml of ethanol to obtain 72.1 g (yield 61%) of 4-(4-propylcyclohexyl)cyclohexanone spiroketal body. Melting point: 52.6°–53.7° C.

Second stage

A suspension of 2.85 g (0.075 mol) of LAH in 80 ml of anhydrous diethyl ether was added dropwise to a solution of 38.4 g (0.14 mol) of anhydrous aluminum chloride in 80 ml of anhydrous diethyl ether and stirred for 30 min. To this solution was added dropwise a solution of 40 g (0.14 mol) of the spiroketal body obtained in the first stage and dissolved in 80 ml of anhydrous diethyl ether, and heated for 3 hours to reflux. Then, under cooling with ice, 20 ml of water was added to destroy an excess amount of the reducing agent and then put in 200 ml of an ice water. It was extracted twice with 400 ml of ethyl acetate, and the organic layer was washed with water twice and dried over anhydrous magnesium sulfate. After the magnesium sulfate was separated, the solvent was distilled off under a reduced pressure, and the residue was recrystallized twice from 40 ml of heptane to obtain 20.7 g (yield 51%) of 4-(4-propylcyclohexyl)-(3-hydroxypropyloxy)cyclohexane. Melting point: 110.4°–111.0° C.

Third stage

DMSO in an amount of 2.13 ml (0.03 mol) was added dropwise to a mixture of 1.74 ml (0.02 mol) of oxalic acid chloride and 40 ml of dichloromethane at −50° C. and stirred for 10 min. While keeping inside of the reaction system at −60°C., this solution was added dropwise with a solution of 2.82 g (0.01 mol) of the 4-(4-propylcyclohexyl)-(3-hydroxypropyloxy)cyclohexane obtained in the second stage and dissolved in 20 ml of dichloromethane and stirred for 1 hour. To this solution was added 14 ml of triethylamine, temperature of the solution was returned to a room temperature, stirred for 15 min, and the solution was added with 80 ml of an aqueous solution saturated with ammonium chloride. The organic layer was separated and dried over anhydrous magnesium sulfate. After the magnesium sulfate was separated, the solvent was distilled off under a reduced pressure, and the residue was subjected to a silica gel column chromatography (eluate: toluene/ethylacetate (9/1)) to obtain 1.93 g of a crude 4-(4-propylcyclohexyl)-(3-oxopropyoxy) cyclohexane. This product was recrystallized from 12 ml of ethanol to obtain 1.3 g (yield 46%) of 4-(4-propylcyclohexyl)-(3-oxopropyloxy)cyclohexane.

Fourth stage

A mixture of 1.3 g (4.6 mmol) of 4-(4-propylcyclohexyl)-(3-oxopropyloxy)cyclohexane obtained in the third stage, 2.0 g (12 mmol) of DAST, and 5 ml of dichloromethane was stirred overnight at a room temperature. The product was put in 20 ml of an ice water and extracted with 20 ml of toluene. The organic layer was washed once with an aqueous solution saturated with potassium carbonate and then twice with water, and dried over anhydrous magnesium sulfate. After the magnesium sulfate was separated, the solvent was distilled off under a reduced pressure, and the residue thus obtained was subjected to a silica gel column chromatography (eluate: toluene) to obtain 0.78 g of a crude 4-(4-propylcyclohexyl)-(3,3-difluoropropyloxy)cyclohexane. This product was recrystallized from 3.5 ml of ethanol in a freezer to obtain 0.51 g (yield 17%) of 4-(4-propylcyclohexyl)-(3,3-difluoropropyloxy)cyclohexane. Several kinds of spectra well supported its structure.

$^1$H-NMR (TMS internal standard) δ (ppm): 5.91 (tt, 1H), 3.56 (t, 2H), 3.05 (m, 1H), 2.31–0.76 (m, 28H)

GC-MS: 302 (M+)

Cr 24.3 SB 53.5 Iso

The following compounds (No. 139 through No. 160) were produced according to the method in Example 4. Each of the compounds are indicated by excerpting parameters $R_1$, Q, and $—O(CH_2)_nCF_2H$ in the same way as described before.

| Compound No. | $R_1$ | I | $—O(CH_2)nCF_2H$ | Phase transition point |
|---|---|---|---|---|
| 139 | $C_2H_5$ | 0 | $—O(CH_2)_2CF_2H$ | |
| 140 | $C_2H_5$ | 0 | $—O(CH_2)_3CF_2H$ | |
| 141 | $C_3H_7$ | 0 | $—O(CH_2)_2CF_2H$ | Cr24.3 SB 53.5 Iso |
| 142 | $C_3H_7$ | 0 | $—O(CH_2)_3CF_2H$ | |
| 143 | $C_3H_7$ | 0 | $—O(CH_2)_4CF_2H$ | |
| 144 | $C_4H_9$ | 0 | $—O(CH_2)_2CF_2H$ | |
| 145 | $C_4H_9$ | 0 | $—O(CH_2)_4CF_2H$ | |
| 146 | $C_5H_{11}$ | 0 | $—O(CH_2)_2CF_2H$ | |
| 147 | $C_5H_{11}$ | 0 | $—O(CH_2)_3CF_2H$ | |
| 148 | $C_5H_{11}$ | 0 | $—O(CH_2)_4CF_2H$ | |
| 149 | $CH_3CH{=}CH(CH_2)_2—$ | 0 | $—O(CH_2)_3CF_2H$ | |
| 150 | $C_2H_5$ | 1 | $—O(CH_2)_2CF_2H$ | |
| 151 | $C_2H_5$ | 1 | $—O(CH_2)_3CF_2H$ | |
| 152 | $C_3H_7$ | 1 | $—O(CH_2)_2CF_2H$ | |
| 153 | $C_3H_7$ | 1 | $—O(CH_2)_3CF_2H$ | |
| 154 | $C_3H_7$ | 1 | $—O(CH_2)_4CF_2H$ | |
| 155 | $C_4H_9$ | 1 | $—O(CH_2)_2CF_2H$ | |
| 156 | $C_4H_9$ | 1 | $—O(CH_2)_4CF_2H$ | |
| 157 | $C_5H_{11}$ | 1 | $—O(CH_2)_2CF_2H$ | |
| 158 | $C_5H_{11}$ | 1 | $—O(CH_2)_3CF_2H$ | |
| 159 | $C_5H_{11}$ | 1 | $—O(CH_2)_4CF_2H$ | |
| 160 | $C_3H_7CH{=}CH—$ | 1 | $—O(CH_2)_3CF_2H$ | |

EXAMPLE 5

Production of 4-(4-pentylcyclohexyl)-(2-fluorobutyloxy) cyclohexane (Compound expressed by the formula (1) wherein $R_1$ is $C_5H_{11}$, X and Y are H, Q is O, m and n are 1, and p is 2. Compound No. 174))

First Stage

While keeping inside of a reaction system at a temperature of lower than 10° C., a solution of 5.24 g (16.3 mmol) of 4-(4-pentylcyclohexyl)-(2-oxobutyloxy)cyclohexane produced in Example 3 and dissolved in 35 ml of THF was added dropwise to a mixture of 0.46 g (12.2 mmol) of LAH and 2.5 ml of THF and further stirred for 5 hours at a room temperature. To this solution, under cooling, were added 5 ml of ethylacetate and then 10 ml of 2N aqueous solution of sodium hydroxide to terminate the reaction. After undissolved products were separated, the solvent was distilled off under a reduced pressure and the residue thus obtained was recrystallized from 15 ml of hexane to obtain 5.0 g (yield 95%) of 4-(4-pentylcyclohexyl)-(2-hydroxybutyloxy) cyclohexane.

Second stage

A mixture of 3.34 g (10 mmol) of 4-(4-pentylcyclohexyl)-(2-hydroxybutyloxy)cyclohexane obtained in the first stage, 1.61 g (10 mmol) of DAST, and 30 ml of dichloromethane was stirred for 2 hours at a temperature of lower than 10° C. The reaction product was put in 50 ml of an ice water and then extracted with 50 ml of toluene. The organic layer was washed once with an aqueous solution saturated with sodium hydrogencarbonate and twice with water, and dried over anhydrous magnesium sulfate. After the magnesium sulfate was separated, the solvent was distilled off under a reduced pressure, and the residue thus obtained was subjected to a silica gel column chromatography (eluate: heptane) to obtain a crude product of 4-(4-pentylcyclohexyl)-(2-fluorobutyloxy)cyclohexane. This product was recrystallized from a mixed solvent of 10 ml of ethanol and 3 ml of benzene in a freezer to obtain 0.64 g (yield 20%) of 4-(4-pentylcyclohexyl)-(2-fluorobutyloxy)cyclohexane. Several kinds of spectra well supported its structure.

The following compounds (No. 161 through No. 207) were produced according to the method in Example 5. Each of the compounds are indicated by excerpting parameters $R_1$, Q, and $—O(CH_2)_nCFH(CH_2)_pH$ in the same way as described before.

| Compound No. | $R_1$ | I | $—O(CH_2)mCFH(CH_2)pH$ |
|---|---|---|---|
| 161 | $C_2H_5$ | 0 | $—OCFH(CH_2)_2H$ |
| 162 | $C_2H_5$ | 0 | $—OCH_2CFH(CH_2)_2H$ |
| 163 | $C_3H_7$ | 0 | $—OCFH(CH_2)_3H$ |
| 164 | $C_3H_7$ | 0 | $—OCFH(CH_2)_4H$ |
| 165 | $C_3H_7$ | 0 | $—OCH_2CFH(CH_2)_2H$ |
| 166 | $C_3H_7$ | 0 | $—OCH_2CFH(CH_2)_3H$ |
| 167 | $C_3H_7$ | 0 | $—O(CH_2)_2CFHCH_3$ |
| 168 | $C_3H_7$ | 0 | $—O(CH_2)_3CFH(CH_2)_2H$ |
| 169 | $C_3H_7$ | 0 | $—O(CH_2)_3CFHCH_3$ |
| 170 | $C_4H_9$ | 0 | $—OCFH(CH_2)_4H$ |
| 171 | $C_4H_9$ | 0 | $—O(CH_2)_3CFHCH_3$ |
| 172 | $C_5H_{11}$ | 0 | $—OCFH(CH_2)_3H$ |
| 173 | $C_5H_{11}$ | 0 | $—OCFH(CH_2)_4H$ |
| 174 | $C_5H_{11}$ | 0 | $—OCH_2CFH(CH_2)_2H$ |
| 175 | $C_5H_{11}$ | 0 | $—OCH_2CFH(CH_2)_3H$ |
| 176 | $C_5H_{11}$ | 0 | $—O(CH_2)_2CFHCH_3$ |
| 177 | $C_5H_{11}$ | 0 | $—O(CH_2)_3CFH(CH_2)_2H$ |
| 178 | $C_5H_{11}$ | 0 | $—O(CH_2)_3CFHCH_3$ |
| 179 | $C_6H_{13}$ | 0 | $—OCFH(CH_2)_4H$ |
| 180 | $C_6H_{13}$ | 0 | $—O(CH_2)_3CFHCH_3$ |
| 181 | $C_3H_7CH=CH—$ | 0 | $—OCH_2CFH(CH_2)_2H$ |
| 182 | $CH_3CH=CH(CH_2)_2—$ | 0 | $—OCH_2CFH(CH_2)_2H$ |
| 183 | $CH_2=CHCH_2OCH_2—$ | 0 | $—OCH_2CFH(CH_2)_2H$ |
| 184 | $CH_3$ | 1 | $—O(CH_2)_2CFH(CH_2)_2H$ |
| 185 | $C_2H_5$ | 1 | $—OCFH(CH_2)_2H$ |
| 186 | $C_2H_5$ | 1 | $—OCH_2CFH(CH_2)_2H$ |
| 187 | $C_3H_7$ | 1 | $—OCFH(CH_2)_3H$ |
| 188 | $C_3H_7$ | 1 | $—OCFH(CH_2)_4H$ |
| 189 | $C_3H_7$ | 1 | $—OCH_2CFH(CH_2)_2H$ |
| 190 | $C_3H_7$ | 1 | $—OCH_2CFH(CH_2)_3H$ |
| 191 | $C_3H_7$ | 1 | $—O(CH_2)_2CFHCH_3$ |
| 192 | $C_3H_7$ | 1 | $—O(CH_2)_3CFH(CH_2)_2H$ |
| 193 | $C_3H_7$ | 1 | $—O(CH_2)_3CFHCH_3$ |
| 194 | $C_4H_9$ | 1 | $—OCFH(CH_2)_4H$ |
| 195 | $C_4H_9$ | 1 | $—O(CH_2)_3CFHCH_3$ |
| 196 | $C_5H_{11}$ | 1 | $—OCFH(CH_2)_3H$ |
| 197 | $C_5H_{11}$ | 1 | $—OCFH(CH_2)_4H$ |
| 198 | $C_5H_{11}$ | 1 | $—OCH_2CFH(CH_2)_2H$ |
| 199 | $C_5H_{11}$ | 1 | $—OCH_2CFH(CH_2)_3H$ |
| 200 | $C_5H_{11}$ | 1 | $—O(CH_2)_2CFHCH_3$ |
| 201 | $C_5H_{11}$ | 1 | $—O(CH_2)_3CFH(CH_2)_2H$ |
| 202 | $C_5H_{11}$ | 1 | $—O(CH_2)_3CFHCH_3$ |
| 203 | $C_6H_{13}$ | 1 | $—OCFH(CH_2)_4H$ |
| 204 | $C_6H_{13}$ | 1 | $—O(CH_2)_3CFHCH_3$ |
| 205 | $C_7H_{15}$ | 1 | $—OCH_2CFH(CH_2)_2H$ |
| 206 | $C_8H_{17}$ | 1 | $—OCH_2CFH(CH_2)_2H$ |
| 207 | $C_9H_{19}$ | 1 | $—OCH_2CFH(CH_2)_2H$ |

EXAMPLE 6

Production of 4-(4-propylcyclohexyl)-(3-fluoropropyloxy) cyclohexane (Compound expressed by the formula (1) wherein $R_1$ is $C_3H_7$, X and Y are H, Q is 0, m is 1, n is 2, and p is 0. Compound No. 211))

First Stage

A mixture of 2.75 g (9.8 mmol) of 4-(4-propylcyclohexyl)-(3-hydroxypropyloxy)cyclohexane obtained in Example 4, 3.14 g (19.6 mmol) of DAST, and 25 ml of dichloromethane was stirred for 5 hours at a room temperature. The reaction product was put in 40 ml of an ice water and extracted with 40 ml of toluene. The organic layer was washed with water twice and dried over anhydrous magnesium sulfate. The magnesium sulfate was separated, the solvent was distilled off under a reduced pressure, and the residue thus obtained was subjected to a silica gel column chromatography (eluate: toluene) to obtain 1.87 g of a crude 4-(4-propylcyclohexyl)-(3-fluoropropyloxy) cyclohexane. This product was recrystallized twice from 6 ml of ethanol in a freezer to obtain 1.60 g (yield 58%) of 4-(4-propylcyclohexyl)-(3-fluoropropyloxy)cyclohexane. Several kinds of spectra well supported its structure.

$^1$H-NMR (TMS internal standard) δ (ppm): 4.53 (dt, 2H), 3.57 (t, 2H), 3.13 (m, 1H), 2.20–0.78 (m, 28H)

GC-MS: 284 (M+)

Cr 22.7 SB 64.1 Iso

The following compounds (No. 208 through No. 229) were produced according to the method in Example 6. Each of the compounds are indicated by excerpting parameters $R_1$, Q, and $—O (CH_2)_nCF_2$ in the same way as described before.

| Compound No. | $R_1$ | I | $—O(CH_2)mCFH_2$ | Phase transition point |
|---|---|---|---|---|
| 208 | $C_2H_5$ | 0 | $—OCH_2CFH_2$ | |
| 209 | $C_2H_5$ | 0 | $—O(CH_2)_2CFH_2$ | |
| 210 | $C_3H_7$ | 0 | $—CCH_2CFH_2$ | Cr 53.4 Iso |
| 211 | $C_3H_7$ | 0 | $—O(CH_2)_2CFH_2$ | Cr 22.7 SB 64.1 Iso |
| 212 | $C_3H_7$ | 0 | $—O(CH_2)_3CFH_2$ | |
| 213 | $C_4H_9$ | 0 | $—OCH_2CFH_2$ | |
| 214 | $C_4H_9$ | 0 | $—O(CH_2)_3CFH_2$ | |
| 215 | $C_5H_{11}$ | 0 | $—OCH_2CFH_2$ | Cr 53.2 SB 68.1 Iso |
| 216 | $C_5H_{11}$ | 0 | $—O(CH_2)_2CFH_2$ | |
| 217 | $CH_2=CHC_2H_4—$ | 0 | $—OCH_2CFH_2$ | |
| 218 | $C_3H_7CH=CH—$ | 0 | $—O(CH_2)_2CFH_2$ | |
| 219 | $C_2H_5$ | 1 | $—OCH_2CFH_2$ | |
| 220 | $C_2H_5$ | 1 | $—O(CH_2)_2CFH_2$ | |
| 221 | $C_3H_7$ | 1 | $—OCH_2CFH_2$ | |
| 222 | $C_3H_7$ | 1 | $—O(CH_2)_2CFH_2$ | |
| 223 | $C_3H_7$ | 1 | $—O(CH_2)_3CFH_2$ | |
| 224 | $C_4H_9$ | 1 | $—OCH_2CFH_2$ | |
| 225 | $C_4H_9$ | 1 | $—O(CH_2)_3CFH_2$ | |
| 226 | $C_5H_{11}$ | 1 | $—OCH_2CFH_2$ | Cr30.4SB 78.1 Iso |
| 227 | $C_5H_{11}$ | 1 | $—O(CH_2)_2CFH_2$ | |
| 228 | $C_3H_7CH=CH—$ | 1 | $—OCH_2CFH_2$ | |
| 229 | $CH_2=CHCH_2OCH_2—$ | 1 | $—O(CH_2)_2CFH_2$ | |

While the clearing point of the compound No. 210 was 53.4° C., it can be understood that the value is higher compared with the clearing point of 46° C. of the known bicyclohexane type compound having the same structure except that the alkoxy group at the end of molecule is not substituted with a fluorine atom (reference is made to Examined Japanese Patent Publication No. 5-020418). Also, while the clearing point of the compound No. 215 was 68.1°

C., it can be understood that the value is higher compared with the clearing point of 63° C. of the known bicyclohexane type compound having the same structure except that the alkoxy group at the end of molecule is not substituted with a fluorine atom (reference is made to Examined Japanese Patent Publication No. 5-020418).

EXAMPLE 7

Production of 4-(4-propylcyclohexyl)-(1,1-difluoro-1-methoxy)cyclohexane (Compound expressed by the formula (1) wherein $R_1$ is $C_3H_7$, X is F, Y is methoxy, Q=0, m, n, and p are 2.(Compound No. 231))

First Stage

A mixture of 26.6 g (0.1 mole) of 4-(4-propylcyclohexyl) cyclohexane carboxylic acid methyl ester produced according to the method for obtaining compound (11) mentioned in scheme (6)–(13), 40.4 g (0.1 mol) of Lawson reagent, and 100 ml of toluene was heated for 71 hours to reflux. Then, the solution was put in 100 ml of an ice water and the organic layer thus separated was washed with water thrice, and dried over anhydrous magnesium sulfate. After the magnesium sulfate was separated, the solvent was distilled off under a reduced pressure, and the residue thus obtained was recrystallized from 50 ml of ethanol to obtain 9.6 g (yield 34%) of a thioester. Melting point: 77.5° C.

Second stage

A mixture of 9.6 g (34 mmol) of the thioester obtained in the first stage, 10.9 g (68 mmol) of DAST, and 50 ml of dichloromethane was stirred for 4 hours at a room temperature. The reaction product was put in 100 ml of an ice water and then extracted with 100 ml of toluene. The organic layer was washed twice with water and dried over anhydrous magnesium sulfate. After the magnesium sulfate was separated, the solvent was distilled off under a reduced pressure, and the residue thus obtained was subjected to a silica gel column chromatography (eluate: heptane) to obtain a crude product of 4-(4-propylcyclohexyl)-(1,1-difluoro-1-methoxy)cyclohexane. This product was recrystallized twice from 5 ml of ethanol in a freezer to obtain 0.58 g (yield 6%) of 4-(4-propylcyclohexyl)-(1,1-difluoromethoxy) cyclohexane. Several kinds of spectra well supported its structure.

$^1$H-NMR (TMS internal standard) δ (ppm): 3.51 (s, 3H), 2.05–0.62 (m, 27H)

GC-MS: 288 (M+)

Cr 51.5 SB 90.8 Iso

It can be understood that the clearing point 90.8° C. mentioned above is considerably higher compared with the clearing point of 52.0° C. of the known bicyclohexane type compound having the same structure except that the methoxy substituted alkyl group at the end of molecule is not substituted with a fluorine atom (reference is made to Examined Japanese Patent Publication No. 62-005415).

The following compounds (No. 230 through No. 251) were produced according to the method in Example 7.Each of the compounds are indicated by excerpting parameters $R_1$, Q, and $-(O)_m(CH_2)_nCF_2OR$ in the same way as described before.

| Compound No. | $R_1$ | I | $-(O)_m(CH_2)_nCF_2OR$ | Phase transition point |
|---|---|---|---|---|
| 230 | $C_2H_5$ | 0 | $-(CH_2)_2CF_2OMe$ | |
| 231 | $C_3H_7$ | 0 | $-CF_2OMe$ | Cr 51.5 SB |

-continued

| Compound No. | $R_1$ | I | $-(O)_m(CH_2)_nCF_2OR$ | Phase transition point |
|---|---|---|---|---|
| | | | | 90.8 Iso |
| 232 | $C_3H_7$ | 0 | $-CF_2OEt$ | |
| 233 | $C_3H_7$ | 0 | $-CH_2CF_2OMe$ | |
| 234 | $C_3H_7$ | 0 | $-O(CH_2)_2CF_2OMe$ | |
| 235 | $C_4H_9$ | 0 | $-CH_2CF_2OMe$ | Cr 5.2 SB 78.1 Iso |
| 236 | $C_4H_9$ | 0 | $-(CH_2)_2CF_2OEt$ | |
| 237 | $C_5H_{11}$ | 0 | $-O(CH_2)_2CF_2OMe$ | |
| 238 | $C_5H_{11}$ | 0 | $-O(CH_2)_3CF_2OMe$ | |
| 239 | $C_5H_{11}$ | 0 | $-CH_2CF_2OMe$ | |
| 240 | $C_3H_7CH=CH-$ | 0 | $-CF_2OEt$ | |
| 241 | $C_2H_5$ | 1 | $-(CH_2)_2CF_2OMe$ | |
| 242 | $C_2H_5$ | 1 | $-CF_2OMe$ | |
| 243 | $C_3H_7$ | 1 | $-CF_2OEt$ | |
| 244 | $C_3H_7$ | 1 | $-CH_2CF_2OMe$ | |
| 245 | $C_3H_7$ | 1 | $-O(CH_2)_2CF_2OMe$ | |
| 246 | $C_4H_9$ | 1 | $-CH_2CF_2OMe$ | |
| 247 | $C_4H_9$ | 1 | $-(CH_2)_2CF_2OEt$ | |
| 248 | $C_5H_{11}$ | 1 | $-O(CH_2)_2CF_2OMe$ | |
| 249 | $C_5H_{11}$ | 1 | $-O(CH_2)_3CF_2OMe$ | |
| 250 | $C_5H_{11}$ | 1 | $-CH_2CF_2OMe$ | |
| 251 | $C_3H_7CH=CH-$ | 1 | $-CF_2OEt$ | |

EXAMPLE 8

Production of 4-(4-(3-butenyl)cyclohexyl)-(3-fluoropropyl) cyclohexane (Compound expressed by the formula (1) wherein $R_1$ is $CH_2=CHCH_2CH_2-$, X and Y are H, Q and m are 0, n is 2, and p is 0. (Compound No. 256))

First Stage

A solution of DAIBAL (0.1 mol) in 100 ml of THF (concentration: 1 mol/liter) was added dropwise to a solution of 30.6 g (0.1 mol) of 2-(4-(4-(3-butenyl)cyclohexyl) cyclohexyl) propionic acid methyl produced according to the method of Unexamined Japanese Patent Publication No. 1-151531 and dissolved in 100 ml of THF at a temperature of lower than −50° C., and stirred for 1 hour at the same temperature. The reaction liquid was put in 100 ml of an aqueous solution saturated with ammonium chloride and then extracted with 200 ml of toluene. The organic layer was washed with water thrice and dried over anhydrous magnesium sulfate. After the magnesium sulfate was separated and the solvent was distilled off under a reduced pressure, the residue was recrystallized from 60 ml of ethanol to obtain 25.5 g (yield 90%) of 4-(4-(3-butenyl)cyclohexyl)-(3-hydroxypropyl)cyclohexane. Several kinds of spectra well supported its structure.

Second stage

A mixture of 2.8 g (10 mmol) of the 4-(4-(3-butenyl) cyclohexyl)-(3-hydroxypropyl)cyclohexane obtained in the first stage, 3.2 g (20 mmol) of DAST, and 20 ml of dichloromethane was stirred for 4 hours at a room temperature. The reaction product was put in 50 ml of an ice water and then extracted with 50 ml of toluene. The organic layer was washed twice with water and dried over anhydrous magnesium sulfate. After the magnesium sulfate was separated, the solvent was distilled off under a reduced pressure, and the residue thus obtained was subjected to a silica gel column chromatography (eluate: toluene), and recrystallized twice from 5 ml of ethanol in a freezer to obtain 0.64 g (yield 23%) of 4-(4-(3-butenyl)cyclohexyl)-(3-fluoropropyl)cyclohexane. Several kinds of spectra well supported its structure.

The following compounds (No. 252 through No. 343) were produced according to the method in Example 8.Each of the compounds are indicated by excerpting parameters $R_1$, Q, and —$(CH_2)_n$CFXH in the same way as described before.

| Compound No. | $R_1$ | I | —$(CH_2)$nCFXH | Phase transition point |
|---|---|---|---|---|
| 252 | $C_3H_7$CH=CH— | 0 | —$CH_2CFH_2$ | SB 85.5 Iso |
| 253 | $CH_3$CH=$CHC_2H_4$— | 0 | —$CH_2CFH_2$ | SB 66.2 Iso |
| 254 | $CH_2$=$CHCH_2OCH_2$— | 0 | —$CH_2CFH_2$ | |
| 255 | $C_2H_5$CH=CH— | 0 | —$(CH_2)_2CFH_2$ | |
| 256 | $CH_2$=$CHC_2H_4$— | 0 | —$(CH_2)_2CFH_2$ | |
| 257 | $CH_3$CH=$CHC_2H_4$— | 0 | —$(CH_2)_2CFH_2$ | |
| 258 | $CH_3$CH=$CHCH_2O$— | 0 | —$(CH_2)_2CFH_2$ | |
| 259 | $CH_2$=$CHC_2H_4O$— | 0 | —$(CH_2)_2CFH_2$ | |
| 260 | $CH_2$=$OHCH_2OCH_2$— | 0 | —$(CH_2)_2CFH_2$ | |
| 261 | $CH_2$=$CHOCH_2$— | 0 | —$(CH_2)_2CFH_2$ | |
| 262 | $CH_2$=$CHCH_2O$— | 0 | —$(CH_2)_2CFH_2$ | |
| 263 | $C_2H_5$CH=CH— | 0 | —$(CH_2)_3CFH_2$ | |
| 264 | $CH_2$=$CHC_2H_4$— | 0 | —$(CH_2)_3CFH_2$ | |
| 265 | $CH_3$CH=$CHC_2H_4$— | 0 | —$(CH_2)_3CFH_2$ | |
| 266 | $CH_3$CH=$CHCH_2O$— | 0 | —$(CH_2)_3CFH_2$ | |
| 267 | $CH_2$=$CHC_2H_4O$— | 0 | —$(CH_2)_3CFH_2$ | |
| 268 | $CH_2$=$CHCH_2OCH_2$— | 0 | —$(CH_2)_3CFH_2$ | |
| 269 | $CH_2$=$CHOCH_2$— | 0 | —$(CH_2)_3CFH_2$ | |
| 270 | $CH_2$=$CHCH_2O$— | 0 | —$(CH_2)_3CFH_2$ | |
| 271 | $CH_2$=$CHC_2H_4$— | 0 | —$(CH_2)_4CFH_2$ | |
| 272 | $CH_3$CH=$CHC_2H_4$— | 0 | —$(CH_2)_4CFH_2$ | |
| 273 | $CH_2$=$CHCH_2OCH_2$— | 0 | —$(CH_2)_4CFH_2$ | |
| 274 | $CH_3$CH=$CHC_2H_4$— | 0 | —$(CH_2)_5CFH_2$ | |
| 275 | $C_2H_5$CH=CH— | 0 | —$CH_2CF_2H$ | |
| 276 | $CH_3$CH=$CHC_2H_4$— | 0 | —$CH_2CF_2H$ | |
| 277 | $CH_2$=$CHCH_2OCH_2$— | 0 | —$CH_2CF_2H$ | |
| 278 | $C_2H_5$CH=CH— | 0 | —$(CH_2)_2CF_2H$ | |
| 279 | $CH_2$=$CHC_2H_4$— | 0 | —$(CH_2)_2CF_2H$ | |
| 280 | $CH_3$CH=$CHC_2H_4$— | 0 | —$(CH_2)_2CF_2H$ | |
| 281 | $CH_3$CH=$CHCH_2O$— | 0 | —$(CH_2)_2CF_2H$ | |
| 282 | $CH_2$=$CHC_2H_4O$— | 0 | —$(CH_2)_2CF_2H$ | |
| 283 | $CH_2$=$CHCH_2OCH_2$— | 0 | —$(CH_2)_2CF_2H$ | |
| 284 | $CH_2$=$CHOCH_2$— | 0 | —$(CH_2)_2CF_2H$ | |
| 285 | $CH_2$=$CHCH_2O$— | 0 | —$(CH_2)_2CF_2H$ | |
| 286 | $C_2H_5$CH=CH— | 0 | —$(CH_2)_3CF_2H$ | |
| 287 | $CH_2$=$CHC_2H_4$— | 0 | —$(CH_2)_3CF_2H$ | |
| 288 | $CH_3$CH=$CHC_2H_4$— | 0 | —$(CH_2)_3CF_2H$ | |
| 289 | $CH_3$CH=$CHCH_2O$— | 0 | —$(CH_2)_3CF_2H$ | |
| 290 | $CH_2$=$CHC_2H_4O$— | 0 | —$(CH_2)_3CF_2H$ | |
| 291 | $CH_2$=$CHCH_2OCH_2$— | 0 | —$(CH_2)_3CF_2H$ | |
| 292 | $CH_2$=$CHOCH_2$— | 0 | —$(CH_2)_3CF_2H$ | |
| 293 | $CH_2$=$CHCH_2O$— | 0 | —$(CH_2)_3CF_2H$ | |
| 294 | $CH_2$=$CHC_2H_4$— | 0 | —$(CH_2)_4CF_2H$ | |
| 295 | $CH_3$CH=$CHC_2H_4$— | 0 | —$(CH_2)_4CF_2H$ | |
| 296 | $CH_2$=$CHCH_2OCH_2$— | 0 | —$(CH_2)_4CF_2H$ | |
| 297 | $CH_3$CH=$CHC_2H_4$— | 0 | —$(CH_2)_5CF_2H$ | |
| 298 | $C_2H_5$CH=CH— | 1 | —$CH_2CFH_2$ | |
| 299 | $CH_3$CH=$CHC_2H_4$— | 1 | —$CH_2CFH_2$ | |
| 300 | $CH_2$=$CHCH_2OCH_2$— | 1 | —$CH_2CFH_2$ | |
| 301 | $C_2H_5$CH=CH— | 1 | —$(CH_2)_2CFH_2$ | |
| 302 | $CH_2$=$CHC_2H_4$— | 1 | —$(CH_2)_2CFH_2$ | |
| 303 | $CH_3$CH=$CHC_2H_4$— | 1 | —$(CH_2)_2CFH_2$ | |
| 304 | $CH_3$CH=$CHCH_2O$— | 1 | —$(CH_2)_2CFH_2$ | |
| 305 | $CH_2$=$CHC_2H_4O$— | 1 | —$(CH_2)_2CFH_2$ | |
| 306 | $CH_2$=$CHCH_2OCH_2$— | 1 | —$(CH_2)_2CFH_2$ | |
| 307 | $CH_2$=$CHOCH_2$— | 1 | —$(CH_2)_2CFH_2$ | |
| 308 | $CH_2$=$CHCH_2O$— | 1 | —$(CH_2)_2CFH_2$ | |
| 309 | $C_2H_5$CH=CH— | 1 | —$(CH_2)_3CFH_2$ | |
| 310 | $CH_2$=$CHC_2H_4$— | 1 | —$(CH_2)_3CFH_2$ | |
| 311 | $CH_3$CH=$CHC_2H_4$— | 1 | —$(CH_2)_3CFH_2$ | |
| 312 | $CH_3$CH=$CHCH_2O$— | 1 | —$(CH_2)_3CFH_2$ | |
| 313 | $CH_2$=$CHC_2H_4O$— | 1 | —$(CH_2)_3CFH_2$ | |
| 314 | $CH_2$=$CHCH_2OCH_2$— | 1 | —$(CH_2)_3CFH_2$ | |
| 315 | $CH_2$=$CHOCH_2$— | 1 | —$(CH_2)_3CFH_2$ | |
| 316 | $CH_2$=$CHCH_2O$— | 1 | —$(CH_2)_3CFH_2$ | |
| 317 | $CH_2$=$CHC_2H_4$— | 1 | —$(CH_2)_4CFH_2$ | |
| 318 | $CH_3$CH=$CHC_2H_4$— | 1 | —$(CH_2)_4CFH_2$ | |
| 319 | $CH_2$=$CHCH_2OCH_2$— | 1 | —$(CH_2)_4CFH_2$ | |
| 320 | $CH_3$CH=$CHC_2H_4$— | 1 | —$(CH_2)_5CFH_2$ | |
| 321 | $C_2H_5$CH=CH— | 1 | —$CH_2CFH_2$ | |
| 322 | $CH_3$CH=$CHC_2H_4$— | 1 | —$CH_2CFH_2$ | |
| 323 | $CH_2$=$CHCH_2OCH_2$— | 1 | —$CH_2CFH_2$ | |
| 324 | $C_2H_5$CH=CH— | 1 | —$(CH_2)_2CFH_2$ | |
| 325 | $CH_2$=$CHC_2H_4$— | 1 | —$(CH_2)_2CFH_2$ | |
| 326 | $CH_3$CH=$CHC_2H_4$— | 1 | —$(CH_2)_2CFH_2$ | |
| 327 | $CH_3$CH=$CHCH_2O$— | 1 | —$(CH_2)_2CFH_2$ | |
| 328 | $CH_2$=$CHC_2H_4O$— | 1 | —$(CH_2)_2CFH_2$ | |
| 329 | $CH_2$=$CHCH_2OCH_2$— | 1 | —$(CH_2)_2CFH_2$ | |
| 330 | $CH_2$=$CHOCH_2$— | 1 | —$(CH_2)_2CFH_2$ | |
| 331 | $CH_2$=$CHCH_2O$— | 1 | —$(CH_2)_2CFH_2$ | |
| 332 | $C_2H_5$CH=CH— | 1 | —$(CH_2)_3CFH_2$ | |
| 333 | $CH_2$=$CHC_2H_4$— | 1 | —$(CH_2)_3CFH_2$ | |
| 334 | $CH_3$CH=$CHC_2H_4$— | 1 | —$(CH_2)_3CFH_2$ | |
| 335 | $CH_3$CH=$CHCH_2O$— | 1 | —$(CH_2)_3CFH_2$ | |
| 336 | $CH_2$=$CHC_2H_4O$— | 1 | —$(CH_2)_3CFH_2$ | |
| 337 | $CH_2$=$CHCH_2OCH_2$— | 1 | —$(CH_2)_3CFH_2$ | |
| 338 | $CH_2$=$CHOCH_2$— | 1 | —$(CH_2)_3CFH_2$ | |
| 339 | $CH_2$=$CHCH_2O$— | 1 | —$(CH_2)_3CFH_2$ | |
| 340 | $CH_2$=$CHC_2H_4$— | 1 | —$(CH_2)_4CFH_2$ | |
| 341 | $CH_3$CH=$CHC_2H_4$— | 1 | —$(CH_2)_4CFH_2$ | |
| 342 | $CH_2$=$CHCH_2OCH_2$— | 1 | —$(CH_2)_4CFH_2$ | |
| 343 | $CH_3$CH=$CHC_2H_4$— | 1 | —$(CH_2)_5CFH_2$ | |

EXAMPLE 9 (Use Example 1)

Nematic liquid crystal composition ZLI-1132 produced by Merck GmbH, comprising a cyanophenylcyclohexane type liquid crystal compound, and having a clearing point of 72.4° C., value of dielectric anisotropy ($\Delta\epsilon$) of 11.0, value of optical anisotropy ($\Delta n$) of 0.137, viscosity of 27.0 cP, and threshold voltage at a cell thickness of 9μ of 1.78 V was added with the compound of Example 6, 4-(4-propylcyclohexyl)-(3-fluoropropyloxy)cyclohexane in an amount of 15% by weight to obtain a nematic liquid crystal composition. Each value of the physical properties were as follows:

Clearing point: 66.6° C., $\Delta\epsilon$: 9.6, $\Delta n$: 0.121, viscosity: 23.6 cP, and threshold voltage at a cell thickness of 8.7μ: 1.70 V

EXAMPLE 10 (Use Example 2)

A nematic liquid crystal composition was obtained in the same procedures as in Example 9 except that the compound of Example 7, 4-(4-propylcyclohexyl)-(1,1-difluoro-1-methoxy) cyclohexane was used in place of the compound of Example 6. Each value of the physical properties were as follows:

Clearing point: 69.1° C., $\Delta\epsilon$: 9.6, $\Delta n$: 0.124, viscosity: 28.2 cP, and threshold voltage at a cell thickness of 8.7μ: 1.75 V

EXAMPLE 11 (Use Example 3) through EXAMPLE 26 (Use Example 18)

Sixteen kinds of nematic liquid crystal compositions were obtained in the same procedure as in Example 9 except that the compound No. 1, 2, 3, 4, 6, 7, 14, 35, 52, 53, 60, 141, 215, 226, 235, or 252 was used. The value of physical properties of each of the compositions were as follows:

EXAMPLE 11 (Compound of No. 1 was used)

Clearing point: 60.5° C., $\Delta\epsilon$: 9.2, $\Delta n$: 0.119, viscosity: 25.3 cP, and threshold voltage at a cell thickness of 8.7μ: 1.59 V

EXAMPLE 12 (Compound of No. 2 was used)

Clearing point: 66.7° C., $\Delta\epsilon$: 9.4, $\Delta n$: 0.122, and viscosity: 25.1 cP

EXAMPLE 13 (Compound of No. 3 was used)

Clearing point: 64.4° C., Δε: 9.3, Δn: 0.119, viscosity: 25.6 cP, and threshold voltage at a cell thickness of 8.7μ: 1.63 V

EXAMPLE 14 (Compound of No. 4 was used)

Clearing point: 65.6° C., Δε: 9.3, Δn: 0.121, viscosity: 26.4 cP, and threshold voltage at a cell thickness of 8.7μ: 1.66 V

EXAMPLE 15 (Compound of No. 6 was used)

Clearing point: 68.9° C., Δε: 9.5, Δn: 0.123, viscosity: 25.6 cP, and threshold voltage at a cell thickness of 8.7μ: 1.75 V

EXAMPLE 16 (Compound of No. 7 was used)

Clearing point: 68.3° C., Δε: 9.6, Δn: 0.122, viscosity: 25.6 cP, and threshold voltage at a cell thickness of 8.8μ: 1.74 V

EXAMPLE 17 (Compound of No. 14 was used)

Clearing point: 68.7° C., Δε: 9.5, Δn: 0.122, viscosity: 24.4 cP, and threshold voltage at a cell thickness of 8.7μ: 1.64 V

EXAMPLE 18 (Compound of No. 35 was used)

Clearing point: 67.4° C., Δε: 9.6, Δn: 0.121, viscosity: 25.7 cP, and threshold voltage at a cell thickness of 8.8μ: 1.72 V

EXAMPLE 19 (Compound of No. 52 was used)

Clearing point: 72.8° C., Δε: 9.4, Δn: 0.123, viscosity: 22.9 cP, and threshold voltage at a cell thickness of 8.7μ: 1.77 V

EXAMPLE 20 (Compound of No. 53 was used)

Clearing point: 71.3° C., Δε: 9.4, Δn: 0.123, viscosity: 23.9 cP, and threshold voltage at a cell thickness of 8.7μ: 1.77 V

EXAMPLE 21 (Compound of No. 60 was used)

Clearing point: 72.3° C., Δε: 9.5, Δn: 0.122, viscosity: 23.6 cP, and threshold voltage at a cell thickness of 8.8μ: 1.81 V

EXAMPLE 22 (Compound of No. 141 was used)

Clearing point: 65.3° C., Δε: 10.0, Δn: 0.120, viscosity: 23.9 cP, and threshold voltage at a cell thickness of 8.8μ: 1.76 V

EXAMPLE 23 (Compound of No. 215 was used)

Clearing point: 67.7° C., Δε: 9.7, Δn: 0.122, viscosity: 24.6 cP, and threshold voltage at a cell thickness of 8.7μ: 1.73 V

EXAMPLE 24 (Compound of No. 226 was used)

Clearing point: 66.4° C., Δε: 9.6, Δn: 0.122, viscosity: 24.9 cP, and threshold voltage at a cell thickness of 8.8μ: 1.74 V

EXAMPLE 25 (Compound of No. 235 was used)

Clearing point: 69.1° C., Δε: 9.6, Δn: 0.124, viscosity: 28.2 cP, and threshold voltage at a cell thickness of 8.7μ: 1.75 V

EXAMPLE 26 (Compound of No. 252 was used)

Clearing point: 66.7° C., Δε: 9.6, Δn: 0.122, viscosity: 22.1 cP, and threshold voltage at a cell thickness of 8.7μ: 1.69 V According to the present invention, when a fluorine atom was introduced in an alkyl or alkoxy group at the end of the molecule in, for example, bicyclohexane type compounds or cyclohexylethylcyclohexane type compounds, clearing point of liquid crystal compositions comprising the compound is considerably raised. Since the compounds of the present invention are also intended to be used as a viscosity decreasing agent, the compounds can usually be mixed with a liquid crystal composition in a mixing ratio of several tens % when the compounds are actually used. Thus, the difference in clearing point of a single compound exactly comes to considerably affect the clearing of compositions. In this sense, development of the compounds of the present invention which have a high clearing point is extremely useful.

Availability in Industry

Liquid crystal compositions are provided which are suitable for use in liquid crystal display devices, have a high clearing point, and have a function of decreasing viscosity. Also, novel liquid crystalline compounds useful as a component of the liquid crystal compositions are provided.

What is claimed is:

1. A liquid crystalline compound expressed by the general formula (1)

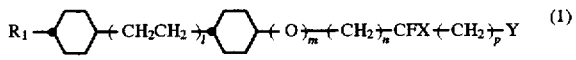

wherein $R_1$ is an alkyl group having 1 to 12 carbon atoms and one $CH_2$ group in the alkyl group may be replaced by oxygen atom or —CH=CH—; X represents hydrogen atom or fluorine atom; Y represents hydrogen atom or alkoxy group having 1 to 5 carbon atoms; l and m independently represent 0 or 1, respectively; and n and p independently represent an integer of 0 to 10, respectively, and when p is 0, n is 2 or more, and when Y is an alkoxy group, X is fluorine atom and p is 0, provided that in no case X is fluorine atom, p is 0, and Y is hydrogen atom when m is 0.

2. A liquid crystalline compound expressed by the general formula (1)

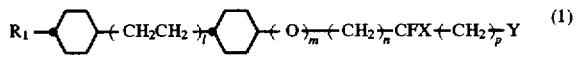

wherein $R_1$ is an alkyl group having 1 to 12 carbon atoms and one $CH_2$ group in the alkyl group may be replaced by oxygen atom or —CH=CH—; X represents a fluorine atom; Y represents an alkoxy group having 1 to 5 carbon atoms; l and m independently represent 0 or 1, respectively; n represents an integer of 2 to 10; and p is 0.

3. A liquid crystalline compound expressed by general formula (1)

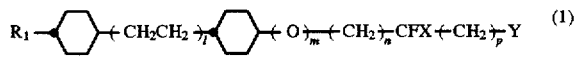

wherein $R_1$ is an alkyl group having 1 to 12 carbon atoms and one $CH_2$ group in the alkyl group may be replaced by oxygen atom or —CH=CH—; X represents a hydrogen atom or flourine atom; Y represents a hydrogen atom or an alkoxy group having 1 to 5 carbon atoms; l represents 0 or 1; m is 0; n represent an integer of 0 to 10; and p is 1.

4. A liquid crystalline compound expressed by the general formula (1)

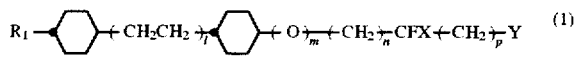

(1)

wherein $R_1$ is an alkyl group having 1 to 12 carbon atoms and one $CH_2$ group in the alkyl group may be replaced by oxygen atom or —CH=CH—; X represents a hydrogen atom or fluorine atom; Y represents a hydrogen atom or an alkoxy group having 1 to 5 carbon atoms; l represents 0 or 1; m is 1; n represents an integer of 0 to 10; and p is 1.

5. The liquid crystalline compound according to claim 1 wherein m is 0.

6. The liquid crystalline compound according to claim 1 wherein m is 1.

7. The liquid crystalline compound according to claim 1 wherein Y is hydrogen atom.

8. The liquid crystalline compound according to claim 5 wherein p is 0.

9. The liquid crystalline compound according to claim 6 wherein p is 0.

10. A liquid crystal composition comprising two or more components at least one of which is a compound according to any one of claims 1, 2, 3, 4, 6, 8.

11. A liquid crystal composition containing, as a first component, at least one compound according to any one of claims 1 to 4, 6, 8, or 2–4 and containing, as a second component, one or more compounds selected from the group consisting of the following general formulas (II), (III), and (IV)

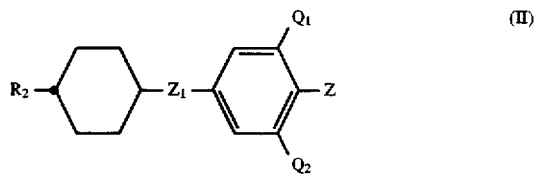

(II)

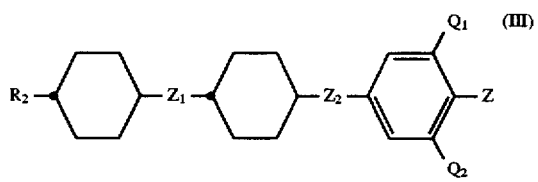

(III)

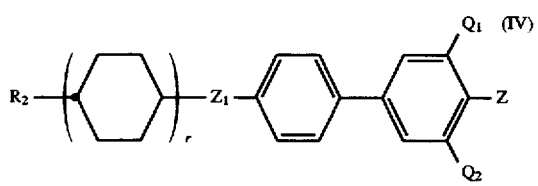

(IV)

wherein $R_2$ represents an alkyl group having 1 to 10 carbon atoms, Z represents F or Cl, $Q_1$ and $Q_2$ independently represent H or F, respectively, r represents 1 or 2, and $Z_1$ and $Z_2$ independently represent —$CH_2CH_2$— or covalent bond.

12. A liquid crystal composition containing, as a first component, at least one compound according to any one of claims 1 to 4, 6, 8, or 2–4 and containing, as a second component, one or more compounds selected from the group consisting of the following general formulas (V), (VI), (VII), (VIII), and (IX)

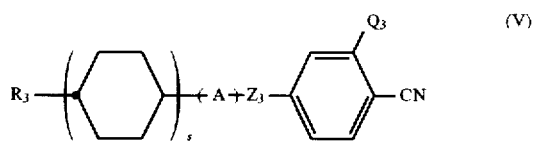

(V)

wherein $R_3$ represents an alkyl group having 1 to 10 carbon atoms or an alkenyl group having 2 to 10 carbon atoms, methylene groups which are not adjacent to each other in these groups may be replaced by oxygen atom, $Z_3$ represents —$CH_2CH_2$—, —COO—, or covalent bond, $Q_3$ represents H or F, A represents a cyclohexane ring, benzene ring, or 1,3-dioxane ring, and s represents 0 or 1.

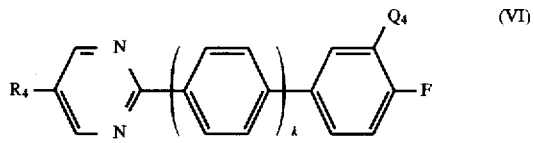

(VI)

wherein $R_4$ represents an alkyl group having 1 to 10 carbon atoms, $Q_4$ represents H or F, and k represents 0 or 1.

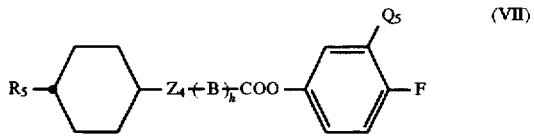

(VII)

wherein $R_5$ represents alkyl group having 1 to 10 carbon atoms, B represents cyclohexane ring or benzene ring, $Q_5$ represents H or F, $Z_4$ represents —COO— or covalent bond, and h represents 0 or 1.

(VIII)

wherein $R_6$ and $R_7$ independently represent an alkyl group, alkoxy group, or alkoxymethyl group each having 1 to 10 carbon atoms, K represents cyclohexane ring, pyrimidine ring, or benzene ring, D represents cyclohexane ring or benzene ring, and $Z_5$ represents —C≡C—, —COO—, —$CH_2CH_2$—, or covalent bond.

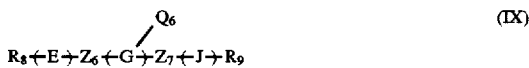

(IX)

wherein $R_8$ represents an alkyl group or alkoxy group each having 1 to 10 carbon atoms, $R_9$ represents an alkyl group, alkoxy group, or alkoxymethyl group each having 1 to 10 carbon atoms, E represents cyclohexane ring or pyrimidine ring, G and J independently represent cyclohexane ring or benzene ring, respectively, $Z_6$ represents —COO—, —$CH_2CH_2$—, or covalent bond, $Z_7$ represents —C≡C—, —COO—, or covalent bond, and $Q_6$ represents H or F.

13. A liquid crystal display device comprising a liquid crystal composition comprising two or more components at least one of which is a compound according to any one of claims 1 to 7, 8, 9 or 2–4.

14. A liquid crystal display device comprising a liquid crystal composition according to claim 10.

15. A liquid crystal display device comprising a liquid crystal composition according to claim 11.

16. A liquid crystal display device comprising a liquid crystal composition according to claim 12.

* * * * *